US005911692A

United States Patent [19]

Hussain et al.

[11] Patent Number: 5,911,692

[45] Date of Patent: Jun. 15, 1999

[54] SPARSE TWO-DIMENSIONAL WIDEBAND ULTRASOUND TRANSDUCER ARRAYS

[75] Inventors: Moayyed Abdulhussain Hussain, Menands; Kenneth Wayne Rigby, Clifton Park; Linda Ann Itani, Ballston Spa, all of N.Y.

[73] Assignee: General Electric Company, Schenectady, N.Y.

[21] Appl. No.: 09/010,046

[22] Filed: Jan. 20, 1998

[51] Int. Cl.$^{6}$ .......... A61B 8/00

[52] U.S. Cl. .......... 600/447

[58] Field of Search .......... 600/444, 447, 600/459; 128/916; 73/625, 626; 367/103, 105

[56] References Cited

U.S. PATENT DOCUMENTS

| | | | |
|---|---|---|---|
| 5,515,060 | 5/1996 | Hussain et al. | 342/376 |
| 5,566,675 | 10/1996 | Li et al. | 600/459 |

OTHER PUBLICATIONS

Rahmat–Samii, "Jacobi–Bessel Analysis of Reflector Antennas with Elliptical Apertures", IEEE Trans. Antennas & Propagation, vol. AP–35, No. 9, Sep. 1987, pp. 1070–1074.

Duan, "A Generalized Three–Parameter (3–P) Aperture Distribution for Antenna Applications", IEEE Trans. Antennas & Propagation, vol. 40, No. 6, Jun. 1992, pp. 697–713.

Hansen, "A One–Parameter Circular Aperture Distribution with Narrow Beamwidth and Low Sidelobes," IEEE Trans. Antennas & Propagation, vol. AP–25, No. 7, Jul. 1976, pp. 477–480.

Taylor, "Design of Line–Source Antennas for Narrow Beamwidth and Low Sidelobes," IRE Trans. Antennas & Propagation, Jan. 1955, pp. 16–28.

Taylor, "Design of Circular Aperture for Narrow Beamwidth and Low Sidelobes," IRE Trans. Antennas & Propagation, Jan. 1960, pp. 17–21.

Hansen, "Tables of Taylor Distributions for Circular Aperture Antennas," IRE Trans. Antennas & Propagation, Jan. 1960, pp. 23–26.

van der Maas, "A Simplified Calculation for Dolph–Tchebycheff Arrays," J. Appl. Phys., vol. 25, No. 1, Jan. 1954, pp. 121–124.

Lo et al., "An Equivalence Theory Between Elliptical and Circular Arrays," IEEE Trans. Antennas & Propagation, Mar. 1965, pp. 247–256.

Bayliss, "Design of Monopulse Antenna Difference Patterns with Low Sidelobes," Bell System Techn. J., May–Jun. 1968, pp. 623–647.

*Primary Examiner*—George Manuel

*Attorney, Agent, or Firm*—Marvin Snyder; Douglas E. Stoner

[57] ABSTRACT

An ultrasonic imaging system employs a thinned array of transducer elements in order to reduce the number of signal processing channels. The transducer elements are reduced in number and then selectively located at grid positions in a pattern which reduces the sidelobe levels produced by the array. Thinning is accomplished by discretizing the aperture of the transducer array in two steps. First, a continuous aperture is discretized as a set of concentric rings. Then each ring is replaced by a set of spaced transducer elements. A zero sampling technique is used to determine the number of elements on each ring.

12 Claims, 29 Drawing Sheets

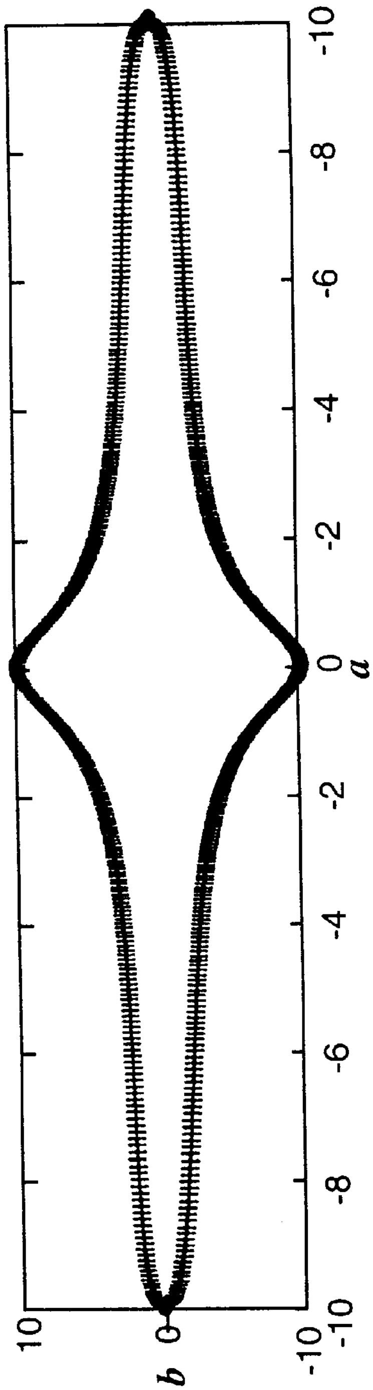
*fig.* 2A
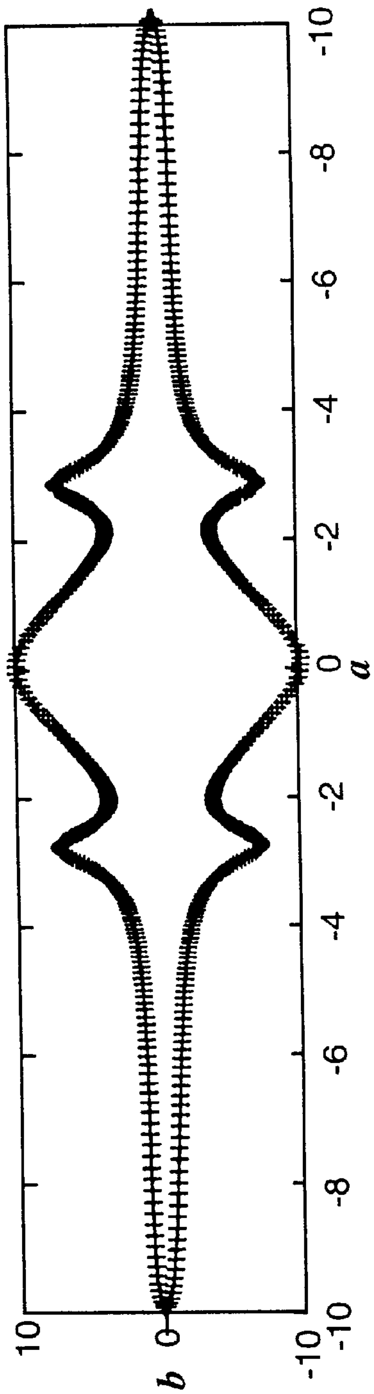
*fig.* 2B
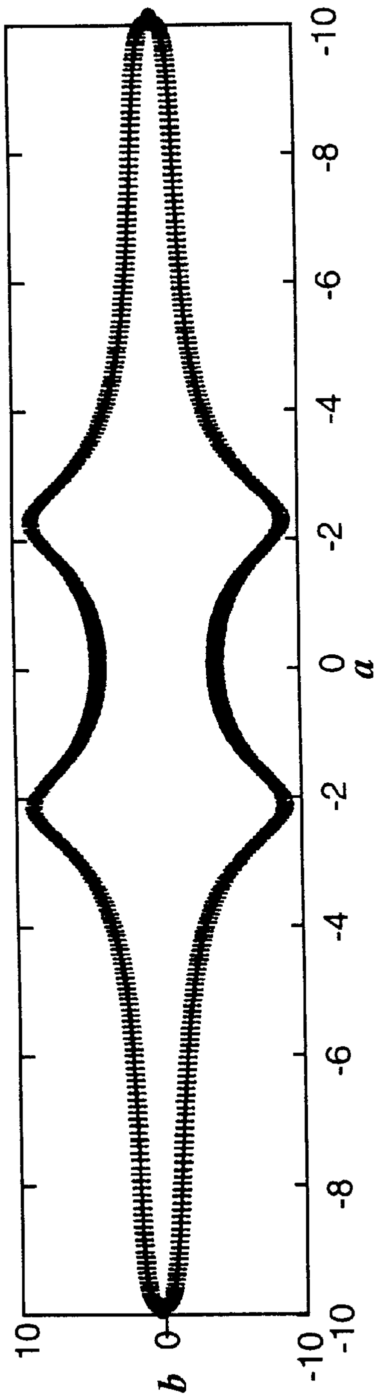
*fig.* 2C

SPARSE TWO-DIMENSIONAL WIDEBAND ULTRASOUND TRANSDUCER ARRAYS

FIELD OF THE INVENTION

This invention relates to medical ultrasound imaging systems having a two-dimensional array of ultrasound transducers, and more particularly, to sparse two-dimensional arrays steerable in azimuth and elevation directions.

BACKGROUND OF THE INVENTION

Conventional ultrasound imaging systems comprise an array of ultrasound transducer elements which transmit an ultrasound beam and receive the reflected beam from the object being studied. For medical ultrasound imaging, the array typically has a multiplicity of transducer elements arranged in a line and driven with separate voltages. By selecting the time delay (or phase) and amplitude of the applied voltages, the individual transducer elements can be controlled to produce ultrasonic waves which combine to form a net ultrasonic wave that travels along a preferred vector direction and is focused at a selected point along the beam. Multiple firings may be used to acquire data representing the same anatomical information. The beamforming parameters of each of the firings may be varied to provide a change in maximum focus or otherwise change the content of the received data for each firing, e.g., by transmitting successive beams along the same scan line with the focal point of each beam being shifted relative to the focal point of the previous beam. By changing the time delay and amplitude of the applied voltages, the beam with its focal point can be moved to scan the object.

The same principles apply when the transducer probe is employed to receive the reflected sound in a receive mode. The voltages produced at the receiving transducer elements are summed so that the net signal is indicative of the ultrasound energy reflected from a single focal point in the object. As with the transmission mode, this focused reception of the ultrasonic energy is achieved by imparting separate time delays (and/or phase shifts) and gains to the signal from each receiving transducer element.

Such scanning comprises a series of measurements in which the steered ultrasonic wave is transmitted, the system switches to receive mode after a short time interval, and the reflected ultrasonic wave is received and stored. Typically, transmission and reception are steered in the same direction during each measurement to acquire data from a series of points along an acoustic beam or scan line. The receiver is dynamically focused at a succession of ranges along the scan line as the reflected ultrasonic waves are received.

Ultrasonic imaging systems are known in which each transducer element is served by an individual analog channel followed by an analog-to-digital converter and one delay chip. Thus, a 128-channel system requires 128 delay chips and all of their associated memory and bus components. The delay chips introduce the time delays required for time delay beamforming. In the receive mode, the signals from all of the transducer elements are time delayed and then summed to form the summed signal representing all of the reflections from a point located at the desired range and steering angle.

It is widely accepted that a two-dimensional array would be advantageous in medical ultrasound imaging. Such an array would be steerable in both the azimuth and elevation directions. One of the limitations on the practicality of two-dimensional arrays is the electronic channel count. Simple brute force extension of conventional systems to such large systems is not practical. Increasing the number of connections to the transducer elements through the coaxial cable to the probe becomes prohibitive. Increasing the electronics of conventional beamforming systems by a factor of four or eight would be expensive and excessively power consuming. By duplexing, it is possible to double the number of effective channels; however, there is a need for further reduction in the number of channels needed to achieve a practical two-dimensional array.

The appearance of landmark papers by T. T. Taylor on the synthesis of linear and circular apertures (in 1955 and 1960) has revolutionized the design procedures for many radars of linear, rectangular or circular apertures which need sidelobe controls. Radar engineers find it fairly routine to incorporate Taylor synthesis in their designs. The Taylor method provides a nearly ideal pattern for realizable illumination of the aperture, and removes the deficiencies of classical Chebyshev arrays. Further, the method has found application in related fields, e.g., pulse compression or filter design, where windowing is essential. The success of the method is due primarily to simplicity of the procedure. The design engineer does not need to investigate the exact mathematical foundation on which the theory is based. It is such precise mathematical analysis that has led to the success of this theory, which uses special functions and asymptotic analysis.

Elliptical apertures and the corresponding analysis have not received great attention despite the wide potential application of elliptical aperture synthesis in modern radar applications, modern communication applications and reflector antennas. This may be due to the unavailability of simple design procedures for synthesis of elliptical arrays or apertures.

Taylor synthesis is outlined in radar handbooks. Advanced books on antenna and radar describe Taylor synthesis for linear arrays as well as for circular arrays to various degrees of sophistication. Some literature for the design of reflectors for communication with projected elliptical shape for earth coverage has appeared. Taylor synthesis can be extended to reduce the number of electrical channels while increasing performance, thereby enhancing imaging capability without additional hardware.

SUMMARY OF THE INVENTION

The invention is an ultrasonic imaging system with a sparse array of transducer elements steerable in two dimensions. The elements are located at selected positions on a regular grid in such a way as to reduce the sidelobe levels produced by the array. The selective location of the transducer elements is hereinafter referred to as "space tapering." The term "space tapering" refers to a deterministic or selective, as opposed to random, placement. The sparse population of the grid positions reduces the number of electronic channels needed to process the signal to and from the transducer elements. The decrease in the population of transducer elements relative to the grid is hereinafter referred to as "thinning." The thinning and space-tapering is accomplished by a flexible, rapid procedure which optimizes the array for all steering angles.

The aperture of the transducer array is discretized into a grid in two steps. First, a continuous aperture is discretized as a set of concentric rings. Next each ring is replaced by a set of transducer elements. To determine the number of elements on each ring, a technique of zero sampling is used.

The array design of the invention is based on analytic solutions of aperture integral equations. Sidelobe control is achieved by controlling the illumination of the aperture. This illumination ultimately corresponds to the density of the elements in the sparse array, with each element of the array having uniform amplitude for maximum efficiency or signal-to-noise ratio. The design goal is to produce sidelobes which are uniform around the main beam and decay asymptotically. Space tapering is accomplished in a manner which improves the sidelobe level relative to that of the fully populated array.

Another aspect of the invention is that the array design is valid for wideband operation centered on the design center frequency. The sidelobe performance does not deteriorate when a pulsed signal is used for ultrasound imaging and, in some cases, is enhanced thereby.

BRIEF DESCRIPTION OF THE DRAWINGS

FIGS. 2A–2C illustrates three noncircular aperture geometries other than elliptical that can be analyzed in accordance with the invention.

FIGS. 12A1–12E are graphs showing the power patterns for both narrowband and wideband operation of the transducer arrays shown in FIGS. 11A–11E respectively.

DETAILED DESCRIPTION OF THE PREFERRED EMBODIMENTS

Although the following description relates to methods for thinning and space tapering ultrasound arrays having circular and elliptical apertures it will be appreciated that the invention has application to apertures of geometries other than circles and ellipses.

In an ultrasound imaging system employing a large number of transducer elements, a circular aperture (for two-dimensional steering) would ideally be chosen to maximize the resolution for all angles, since resolution is roughly proportional to the inverse of the aperture size. But for a reasonable number of elements, the diameter of a circular array is too small. The relationship between the number of elements N and the diameter 2*a* of a circular probe is given by $$\frac{4\pi a^2}{\lambda^2} = N \tag{1}$$

where λ is the ultrasound wavelength, and the area of each element is $(\lambda/2)^2$. If N=512, then 2*a* is about 14λ. Typical one-dimensional ultrasound arrays have aperture widths of 50λ to 100λ, so that an aperture width of 14λ is not adequate. Hence there is a need for thinning or space tapering of transducer elements forming the aperture.

If the aforementioned circular aperture is thinned by 75%, i.e., only every fourth location on a rectangular grid is populated by a transducer element (as opposed to a fully-populated grid wherein each grid point is occupied by a transducer element), then the aperture width 2*a* is about 28λ, which is still inadequate for medical ultrasound imaging systems.

One solution is to replace the circular aperture by an elliptical aperture, which allows increased resolution in one dimension at the expense of decreased resolution in the other. The area of an ellipse with width 2*a* and height 2*b* is πab. If we choose, for example, an aspect ratio b/a=¼, then the area of such an ellipse ($\pi a^2/4$) is one-fourth the area of a circle whose diameter is the width of the ellipse. Since the number of elements required to fully populate an array is proportional to the area of the array, such an elliptical array requires only one-fourth as many elements as the corresponding circular array. Alternately, for the same number of elements, such an elliptical array would be $\sqrt{4}=2$ times wider than the corresponding circular array (but with half the height). For the example above with 75% thinning and 512 elements, this elliptical array would have width of about 52λ. This example, although trivial, illustrates the need for thinning—if possible, to a circular array or, in the alternative, to an elliptical array.

Figure 1:
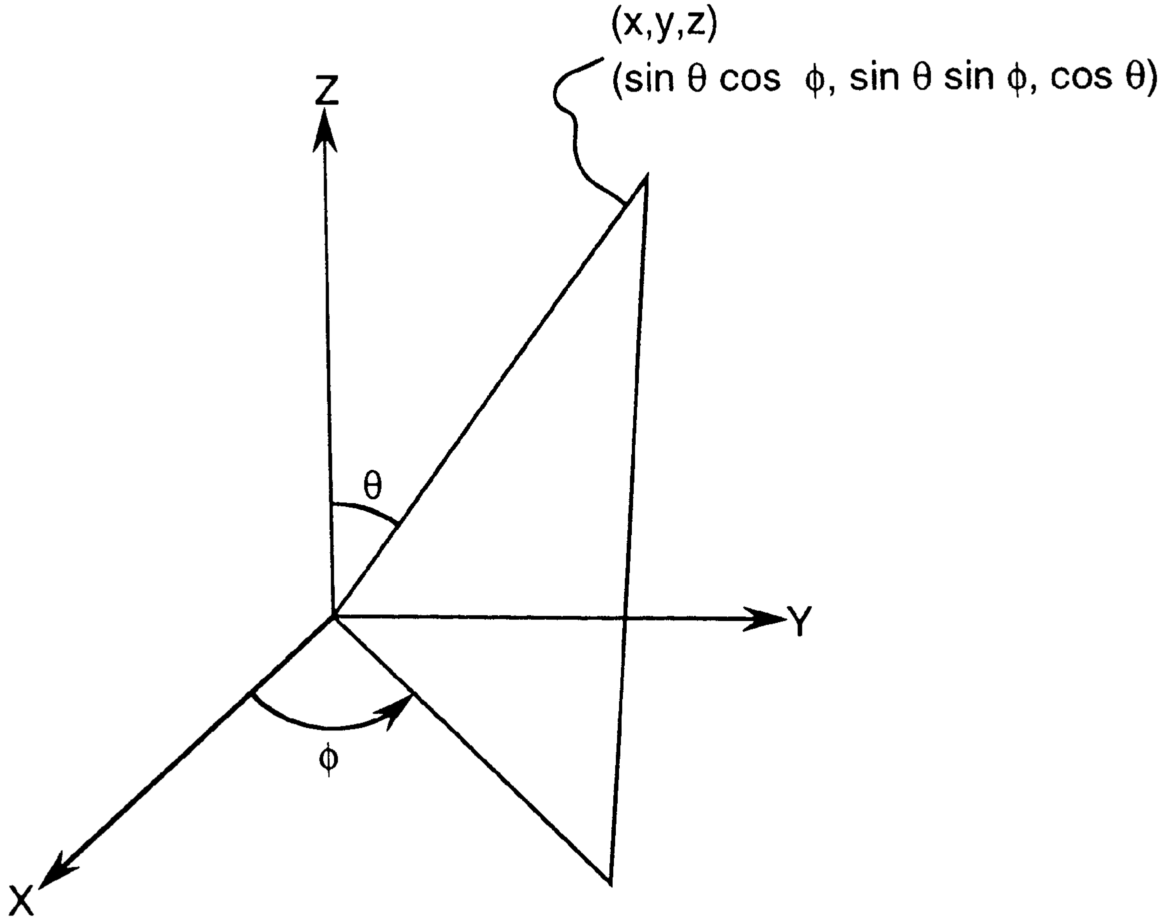
FIG. 1 illustrates the spherical coordinates adopted for the calculations that aid in understanding the invention.

In accordance with phased array theory, consider N transducer elements located at $x_n$, $y_n$ (n=1, . . . , N) along a closed curve, for example, an ellipse. Assume that each element has unit illumination. In the event of an incoming ultrasound beam impinging on the array from the direction (θ, ϕ) as shown in FIG. 1, with the center frequency wavelength λ, the array response is given by $$E(\theta, \varphi) = \sum_{n=1}^{N} e^{\frac{2\pi j}{\lambda}(T_x x_n + T_y y_n)} \tag{2}$$

where the field quantities are given by $T_x$=sin θ cos ϕ and $T_y$=sin θ sin ϕ. For simplicity of presentation, the invariant transformation described in detail by T. Y. Lo and H. C. Hsuan, "An equivalence theory between elliptical and circular arrays," IEEE Trans. Antennas and Propagation, March 1965, pp. 247–253, will be used. This theory enables solutions for a wide variety of geometries to be obtained by mapping them onto a circle. It can be seen from Eq. (2) that the response E(θ, ϕ) remains invariant if $$T_x x_n + T_y y_n = T'_x x'_n + T'_y y'_n \tag{3}$$

where unprimed and primed quantities correspond to the actual and circular geometry respectively. To illustrate the method, consider an elliptical geometry with a, b as the major and minor axes, respectively, mapped onto a circular geometry. The method, however, is quite general and can be used to analyze any geometry as long as it can be mapped onto a circle. FIGS. 2A–2C show three geometries where the method can be applied.

The left-hand side of Eq. (3) may be rewritten in matrix form as $$[x_n\, y_n]\begin{bmatrix} T_x \\ T_y \end{bmatrix} = [x_n\, y_n]\begin{bmatrix} 1 & 0 \\ 0 & \tau \end{bmatrix}\begin{bmatrix} 1 & 0 \\ 0 & t \end{bmatrix}\begin{bmatrix} T_x \\ T_y \end{bmatrix} \tag{4}$$

where τ=1t=a/b, and hence the inner matrix product in Eq. (4) is an identity matrix.

From the right-hand side of Eq. (3) and comparing with Eq. (4), for the invariance the transformation is $x'_n x_n$ $y'_n = \tau y_n$ $T'_x = T_x$ $$T'_y = T_y \tag{5}$$

The source and field angles may be defined as $$\Phi'_n = \tan^{-1}\left(\frac{y'_n}{x'_n}\right) = \tan^{-1}\left(\frac{\tau y_n}{x_n}\right) = \tan^{-1}(\tau\tan\Phi_n) \tag{6a}$$

$$\varphi' = \tan^{-1}\left(\frac{T'_y}{T'_x}\right) = \tan^{-1}\left(t\frac{T_y}{T_x}\right) = \tan^{-1}(t\tan\theta). \tag{6b}$$

Further let $x'_n a \cos\Phi'_n$ $y'_n = a \sin \Phi'_n$ $T'_x R'\cos\phi'$ $T'_y = R'\sin\phi'$ where $$a = \sqrt{x_n'^2 + y_n'^2}$$

$$R' = \sqrt{T_x'^2 + T_y'^2}$$

Hence Eq. (3) becomes $$x'_n T'_x + y'_n T'_y = a\sqrt{1-\kappa^2\sin^2\varphi}\,\sin\theta\cos(\varphi' - \Phi'_n) \tag{8}$$

where $\kappa^2=1-t^2=(1-b^2/a^2$. Hence Eq. (2) becomes $$E(\theta,\varphi) = \sum_{n=1}^{N} e^{\frac{2\pi j}{\lambda}\left(a\sqrt{1-\kappa^2\sin^2\varphi}\,\sin\theta\right)\cos(\varphi'-\Phi'_n)}. \tag{9}$$

If the elements are located in such a way that their angular positions in the transformed plane are equally spaced, then their angular positions $\Phi_n$ in untransformed coordinates are $$\Phi_n = \tan^{-1}\left(\frac{1}{\tau}\tan\left(\frac{2\pi(n-1)}{N}\right)\right) \tag{10}$$

where n=1, . . . , N. The element locations are then given by $$x_n = \frac{b\cos\Phi_n}{\sqrt{1-\kappa^2\cos^2\Phi_n}} \tag{11a}$$

$$y_n = \frac{b\sin\Phi_n}{\sqrt{1-\kappa^2\cos^2\Phi_n}}. \tag{11b}$$

If the number of elements N is large and Eqs. 10, 11a and 16 are true, then Eq. (9) can be approximated by $$E(\theta,\varphi) = NJ_0\left(\frac{2\pi}{\lambda}a\sqrt{1-\kappa^2\sin^2\varphi}\,\sin\theta\right). \tag{12}$$

where $J_o(x)$ is the Bessel function of order zero.

Figure 3A:
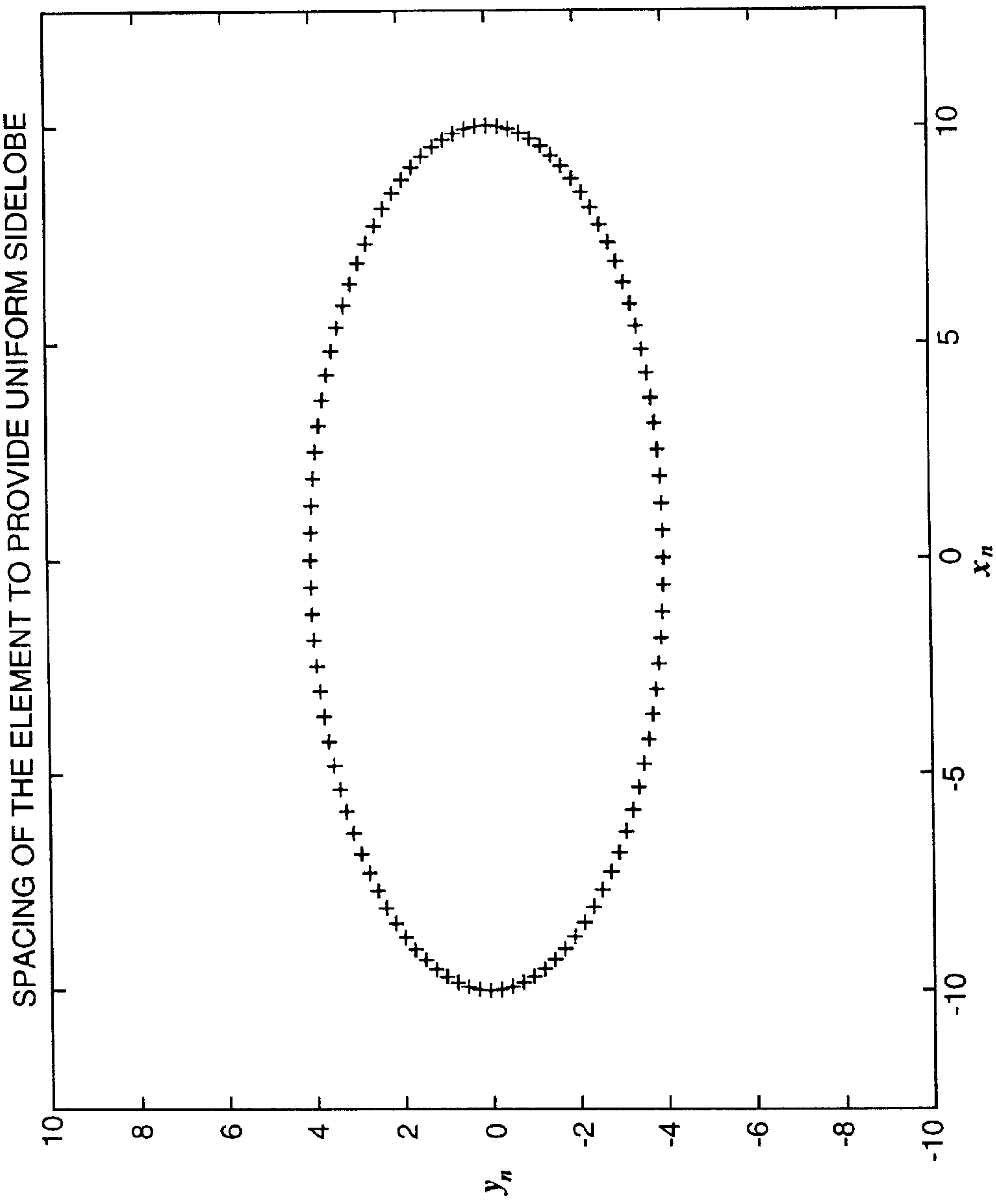
FIG. 3A illustrates the calculated element positions for an elliptical ring geometry in accordance with a preferred embodiment of the invention.
Figure 3B:
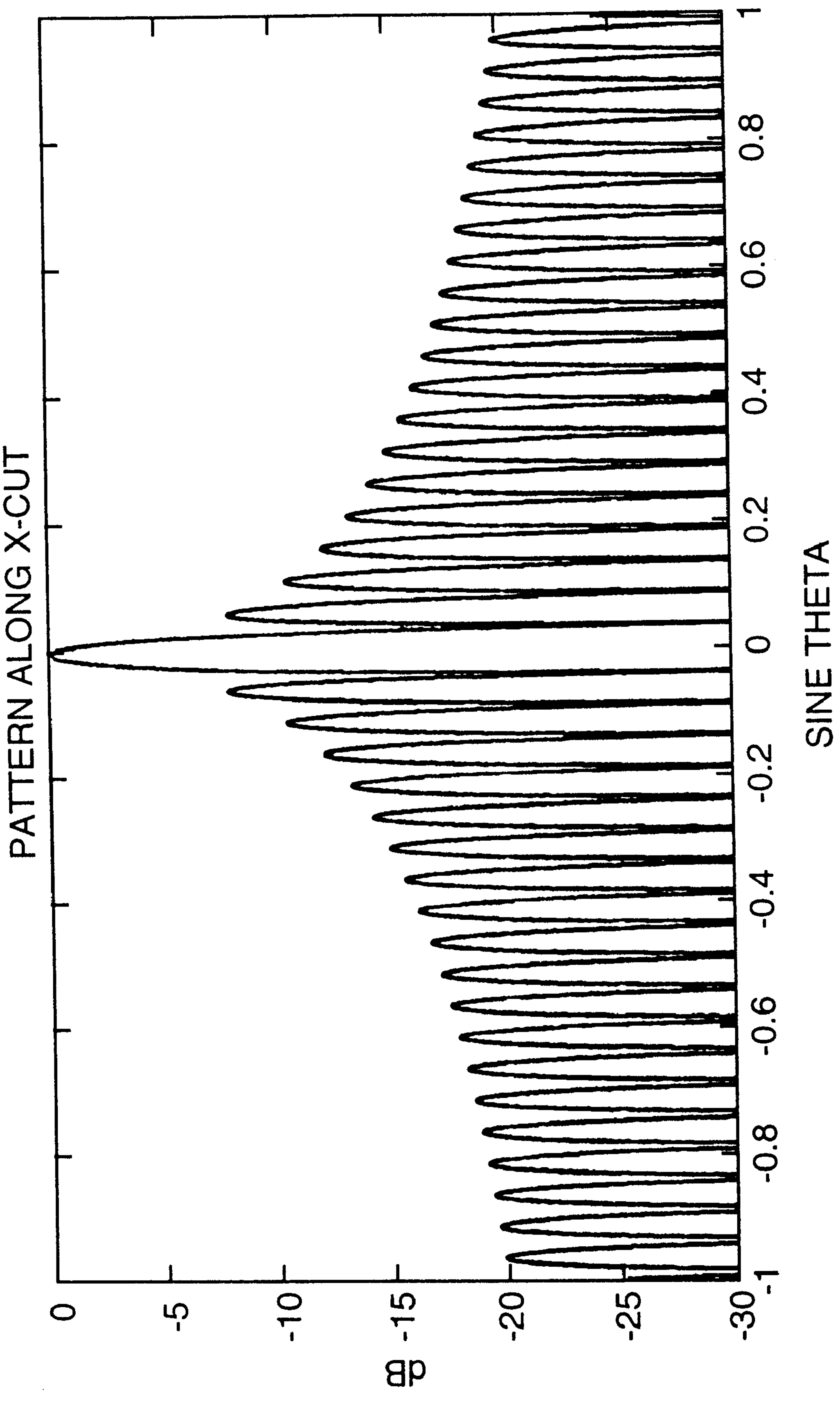
FIGS. 3B–3D show aspects of the power pattern for a discrete set of elements arranged in the elliptical pattern shown in FIG. 3A.
Figure 3C:
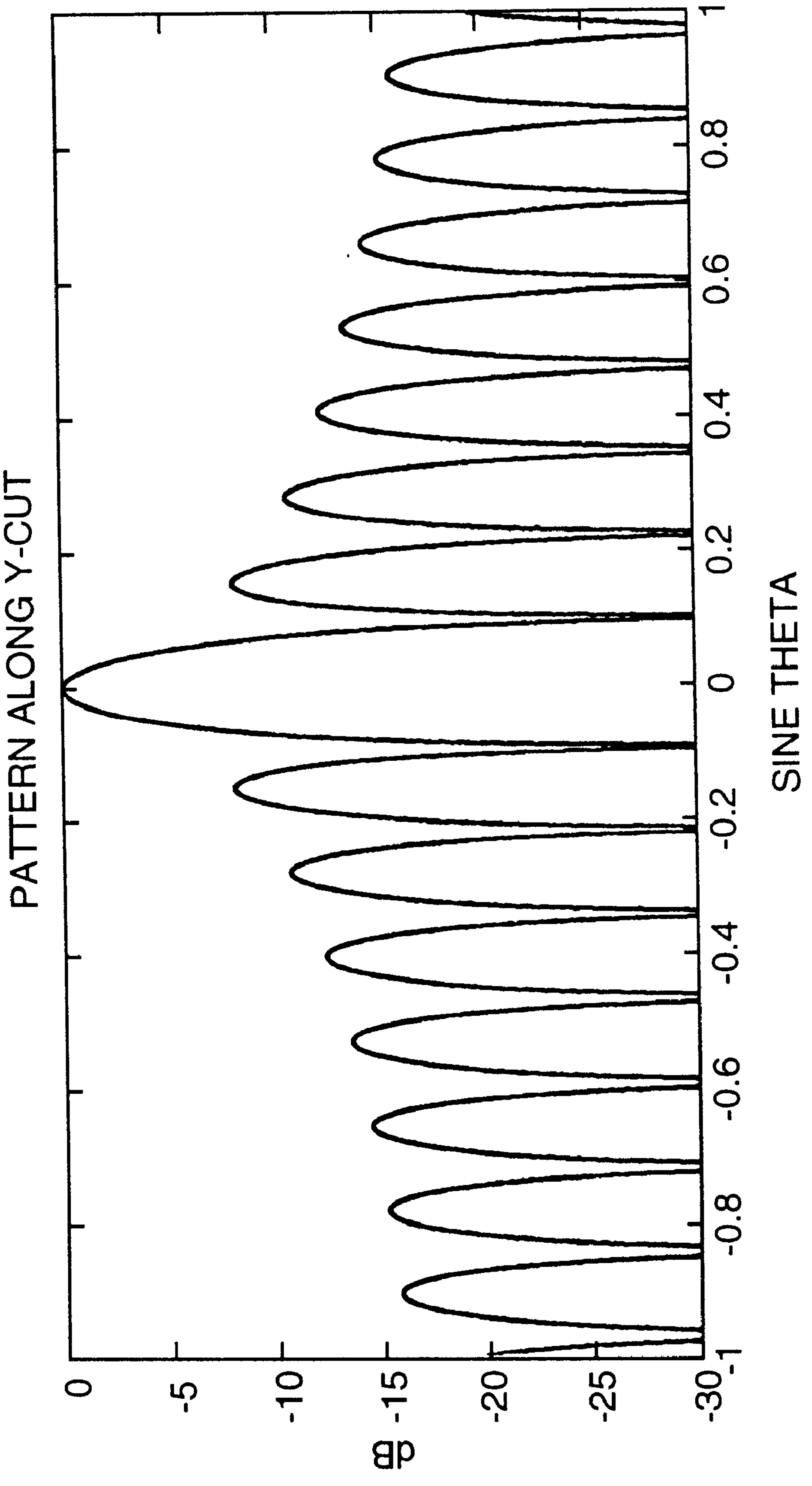
Figure 3D:
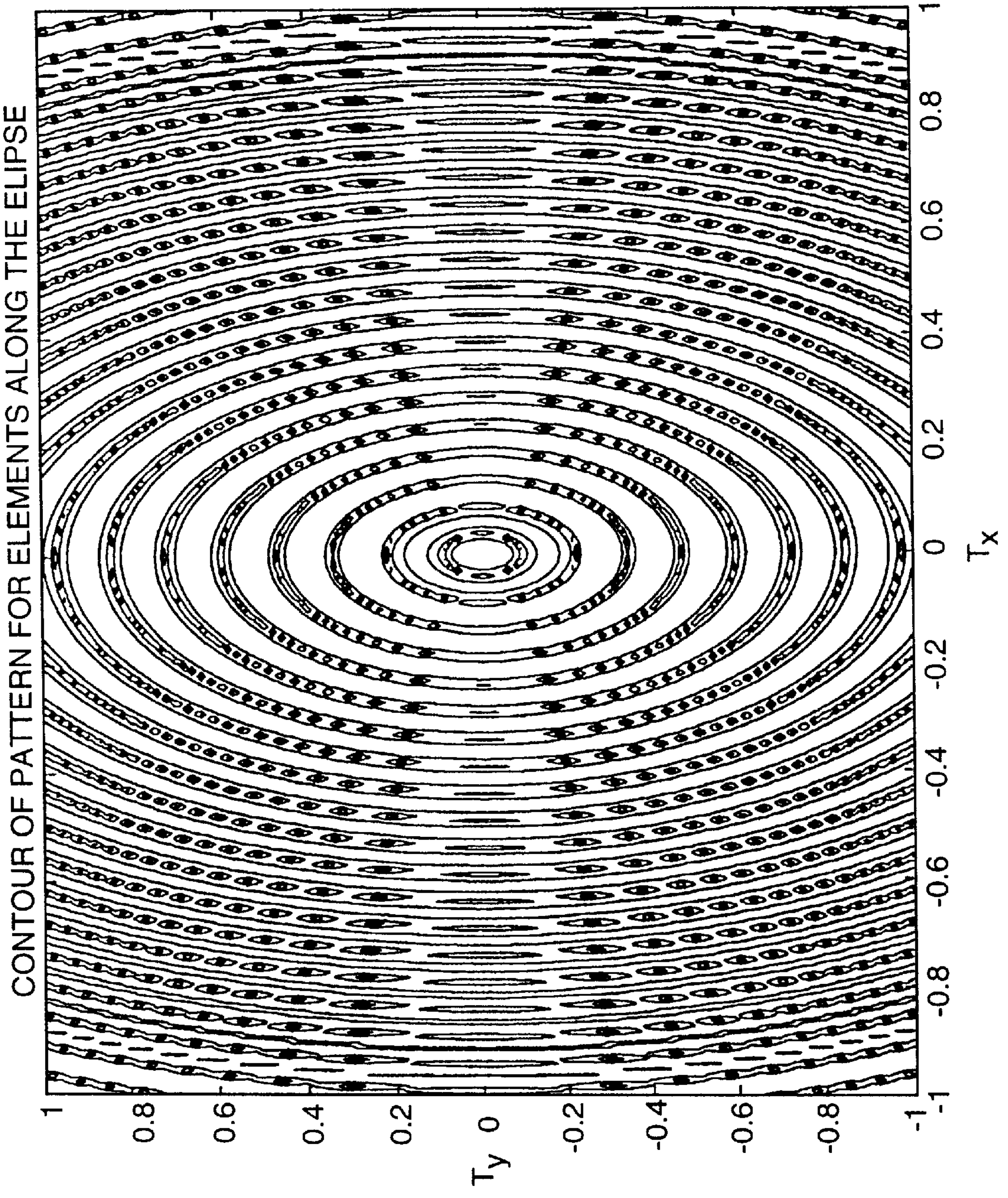

For illustration, the locations of elements on the ellipse are plotted from Eqs. (11a) and (11b) in FIG. 3A. As can be seen in FIG. 3A, the elements are spaced unequally along the ellipse. The corresponding response pattern along the x and y axes are plotted in FIG. 3B and 3C, respectively. FIG. 3D shows the contour pattern. It can be appreciated that the design method of the present invention produces a response pattern which has the symmetry of the array. This elliptical symmetry allows use of the zero sampling method for circular arrays disclosed in U.S. Pat. No. 5,515,060 with the modifications outlined below.

Equation (12) is the solution for a single elliptical ring. Consider a fully populated elliptical aperture which is discretized as a set of M concentric elliptical rings, where the m-th ring has a major axis $a_m$ and a minor axis $b_m$. Further, let each ratio $b_m/a_m$ be the same for all rings and let $N_m$ be the number of elements on the m-th ring. Then from Eq. (12), the response for the set of elliptical rings becomes $$E(\theta,\varphi) = \sum_{m=1}^{M} N_m J_0\left(\frac{2\pi}{\lambda}a_m\sqrt{1-\kappa^2\sin^2\varphi}\,\sin\theta\right) \tag{13}$$

Figure 4:
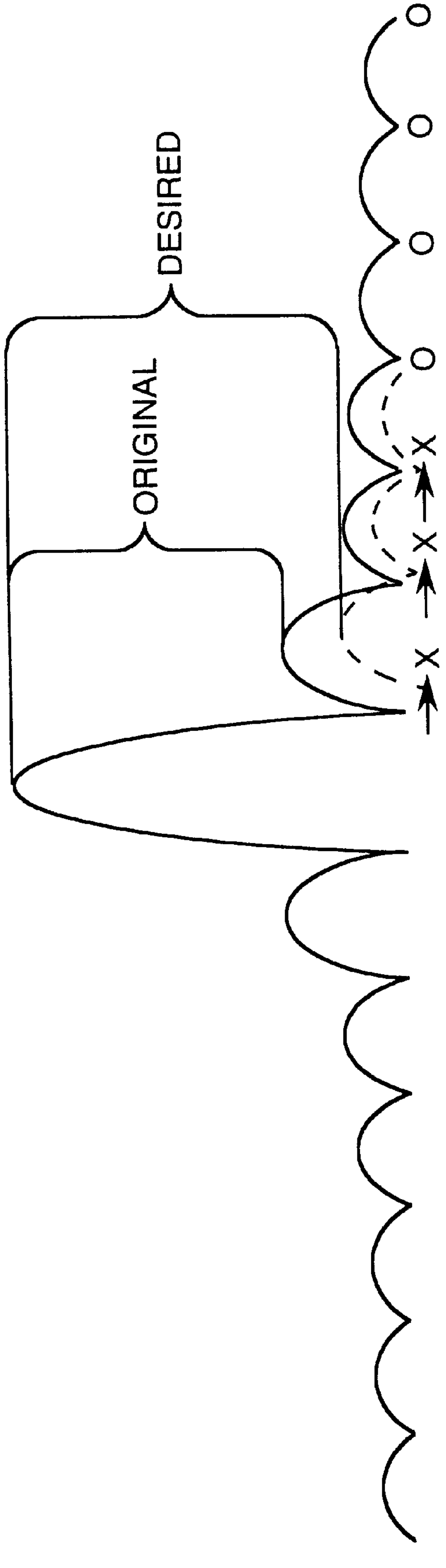
FIG. 4 shows the process of sidelobe control by zero sampling in accordance with the present invention.

The objective is to find $N_m$ (m=1, . . . , M), the number of elements in the m-th ring. Equation (13) has the property that the sidelobes have the same elliptical symmetry as the array. Hence for a fixed $\phi=\phi_0$, Eq. (13) can be shown to be equivalent to the Taylor synthesis problem where the number of elements $N_m$ on the elliptical ring corresponds to the illumination on the m-th ring. The idea of zero sampling for a $\phi=\phi_0$ cut is illustrated schematically in FIG. 4. Since the Taylor method is well known, for simplicity the stretched zeros of Taylor analysis are used. The method can be explained as follows. First select the number of the rings M. M is usually twice the aperture radius in units of wavelengths. Then select $\bar{n}$, the number of sidelobes to be controlled. Typically $\bar{n}$ is 6 to 8. Select R, the ratio of the mainlobe power level to design sidelobe level. Typically R is 40 dB. If R is very large, the far sidelobes will deteriorate. Since far sidelobes are controlled by the total number of elements, an acceptable compromise value of R can be easily selected to keep the root-mean-square (RMS) value of the sidelobes nearly uniform. Compute A from $$A = \frac{\cosh^{-1} R}{\pi}. \tag{14}$$

The stretching parameter for the near-in zeros of the pattern is $$\sigma = \frac{\mu_{\bar{n}}}{\sqrt{(\bar{n} - 0.5)^2 + A^2}} \tag{15}$$

where $\mu_i$ is the i-th zero of the first derivative of the Bessel function of order zero. The Taylor zeros are given by $$\omega_i = \sigma\sqrt{(i - 0.5)^2 + A^2} \tag{16}$$

for i=1, . . . , $\bar{n}$−1, and $$\omega_i \mu_i \tag{17}$$

for i=$\bar{n}$, . . . , M−1. Define a function g $$g = \frac{2a_M \sin\theta}{\lambda}\sqrt{1 - \kappa^2 \sin^2\varphi} \tag{18}$$

where $a_M$ is the major axis of the aperture. The function g will be recognized as part of the argument of the Bessel function in Eq. (13). It will be appreciated that Eq. (18) would be substantially different for a circular aperture. This function must be modified for different geometries.

Defining the non-dimensional radius $a_m/a_M = \gamma_M$, Eq. (13) may be rewritten as follows:

$$E(\theta, \varphi) = \sum_{m=1}^{M} N_m J_0(\pi g \gamma_m). \tag{19}$$

Form the following set of M-1 homogeneous equations by substituting g=$\omega_i$, for i=1, . . . , M−1, and setting E(θ, ϕ) equal to zero:

$$O = N_1 J_0(\pi\omega_i\gamma_1) + N_2 J_0(\pi\omega_i\gamma_2) + \ldots + N_M J_0(\pi\omega_i\gamma_M) \tag{20}$$

where i=1, . . . , M−1. Moving the first term on the right to the left side and dividing both sides by $N_1$, the number of elements on the first ring, the following set of equations is obtained:

$$J_0(\pi\omega_i\gamma_1) = -\frac{N_2}{N_1}J_0(\pi\omega_i\gamma_2) - \cdots - \frac{N_M}{N_1}J_0(\pi\omega_i\gamma_M). \tag{21}$$

These (M−1) equations are solved for the ratios $N_2/N_1$, $N_3/N_1$, . . . , and $N_M/N_1$. The value $N_1$ is determined by the total number of desired elements in the array, $$\sum_{m=1}^{M} N_m.$$

Each $N_m$ must then be rounded to the nearest integer value.

Figure 5A:
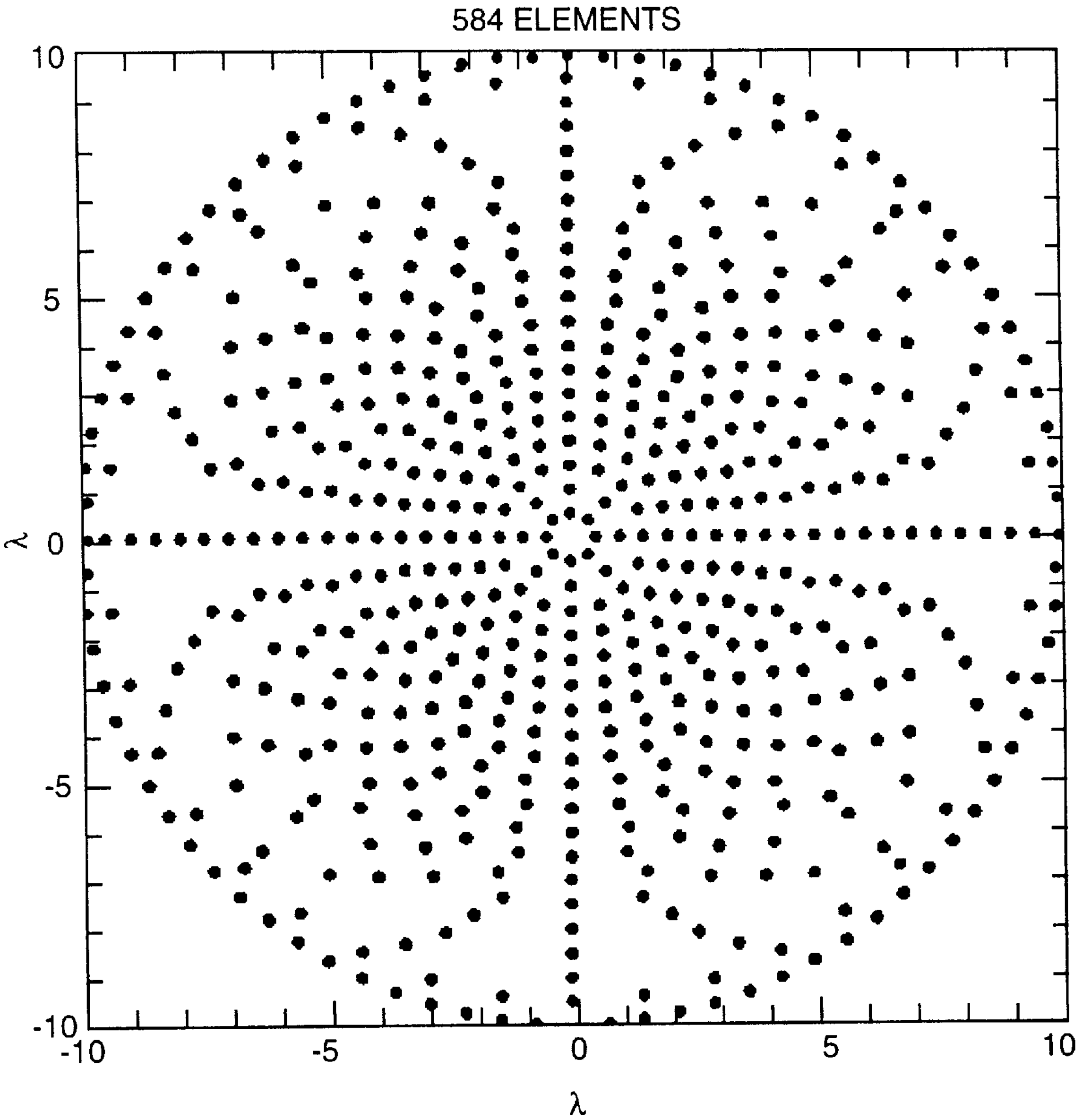
FIGS. 5A–5C depict the layout of transducer elements in a sparse array for a circular aperture having 584, 428 and 280 elements, respectively, in accordance with the invention.
Figure 5B:
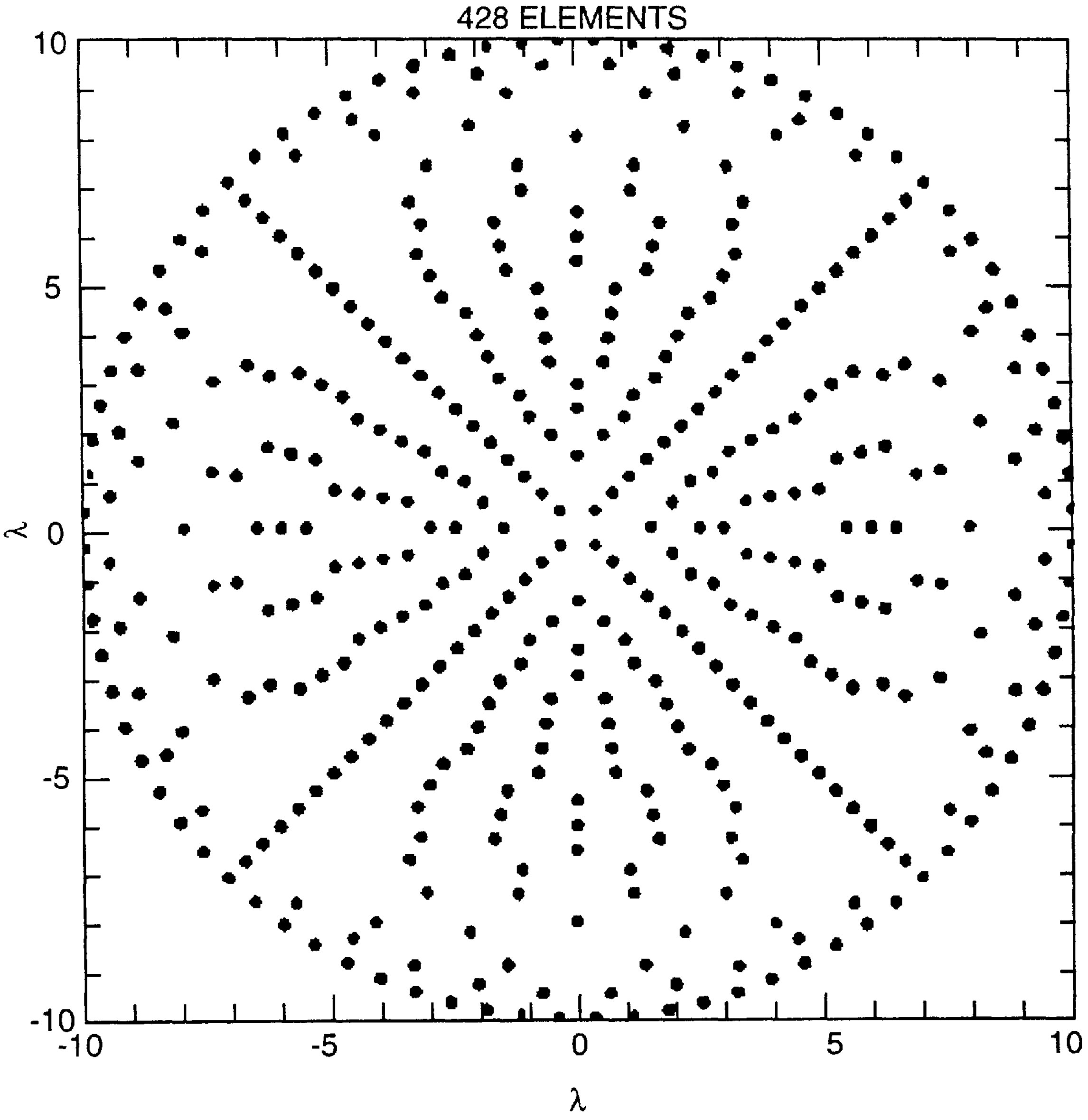
Figure 5C:
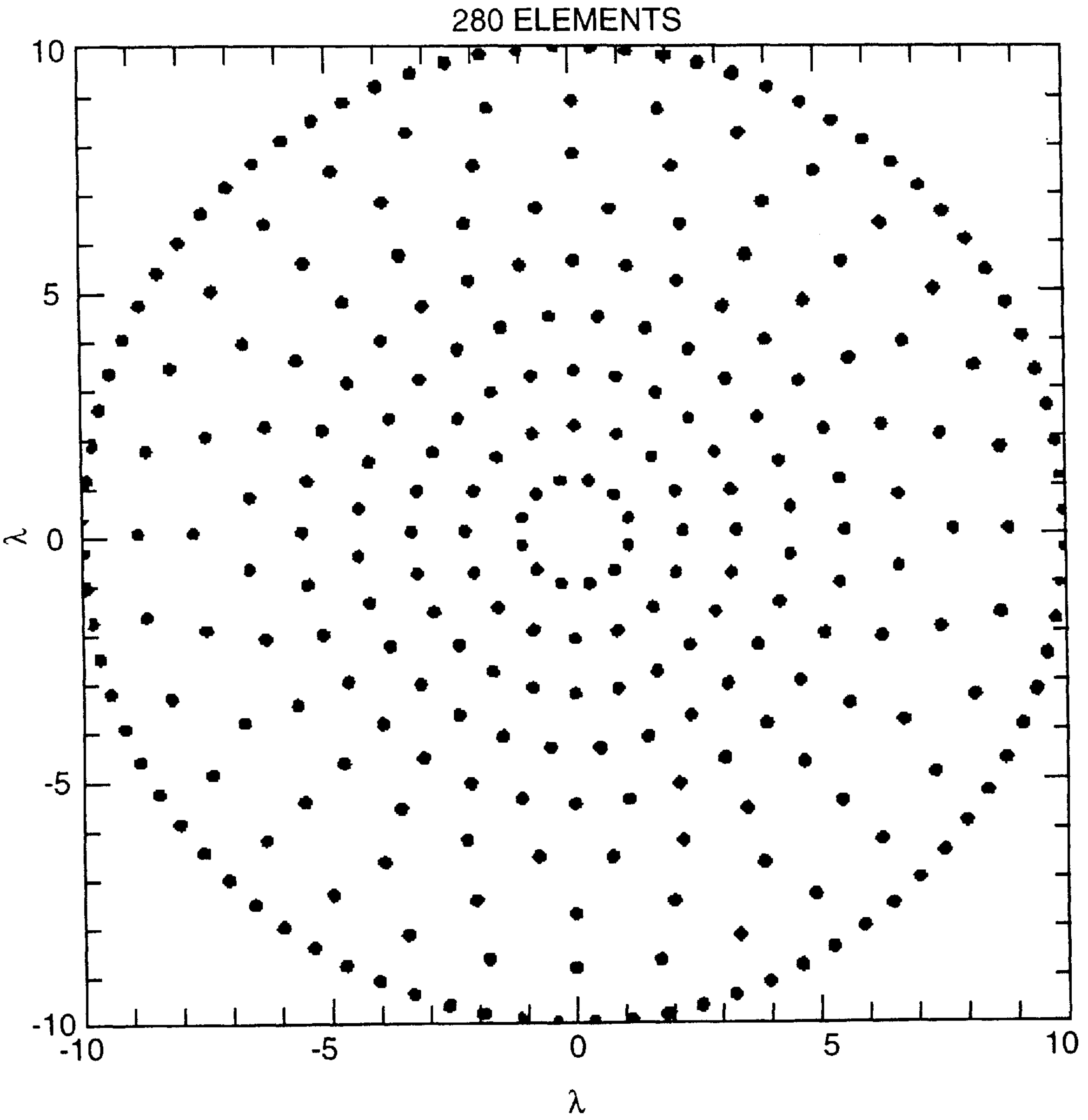

Based on the above algorithm, three examples of thinning are shown in FIGS. 5A–5C. The thinned transducer array shown in FIG. 5A has 584 elements; that shown in FIG. 5B has 428 transducer elements; and that shown in FIG. 5C has 280 elements.

The foregoing analysis was performed at a single frequency, i.e., a single λ. The rings were spaced at ½λ intervals. In practice, λ is taken to be the wavelength at the center frequency. The analysis only involves amplitude control, corresponding to the number of elements located on each ring; no phases were perturbed or controlled. Hence except for the spacing, the above analysis is nearly independent of frequency. Simulation shows that the sidelobe property of space tapering is still maintained under a very wideband operation.

Figure 10:
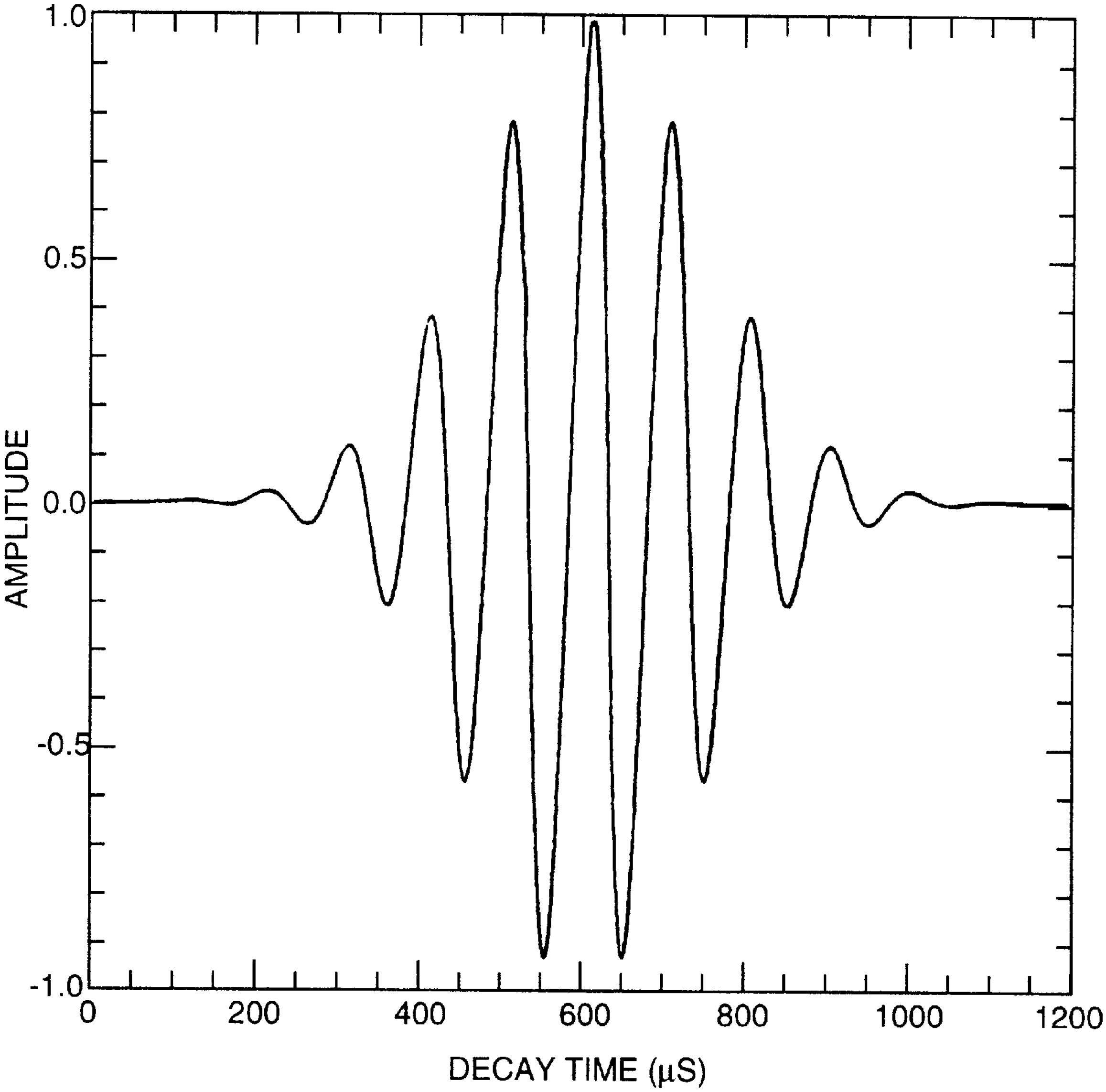
FIG. 10 is a typical pulse used for simulation.
Figure 11A:
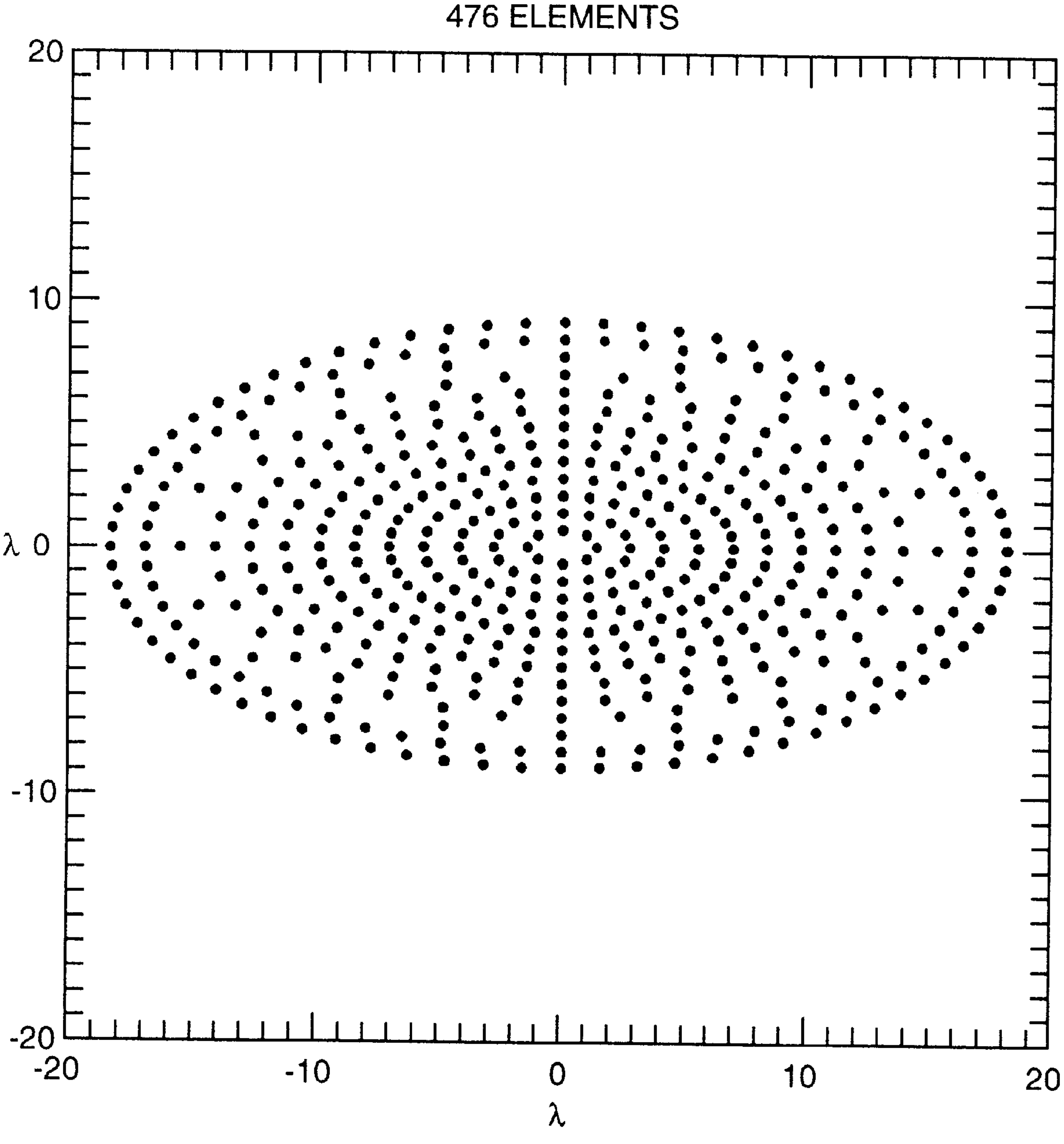
FIGS. 11A–11E depict the transducer element positions in a sparse array for an elliptical aperture having 476, 420, 368, 308 and 264 elements, respectively, in accordance with the invention.
Figure 11B:
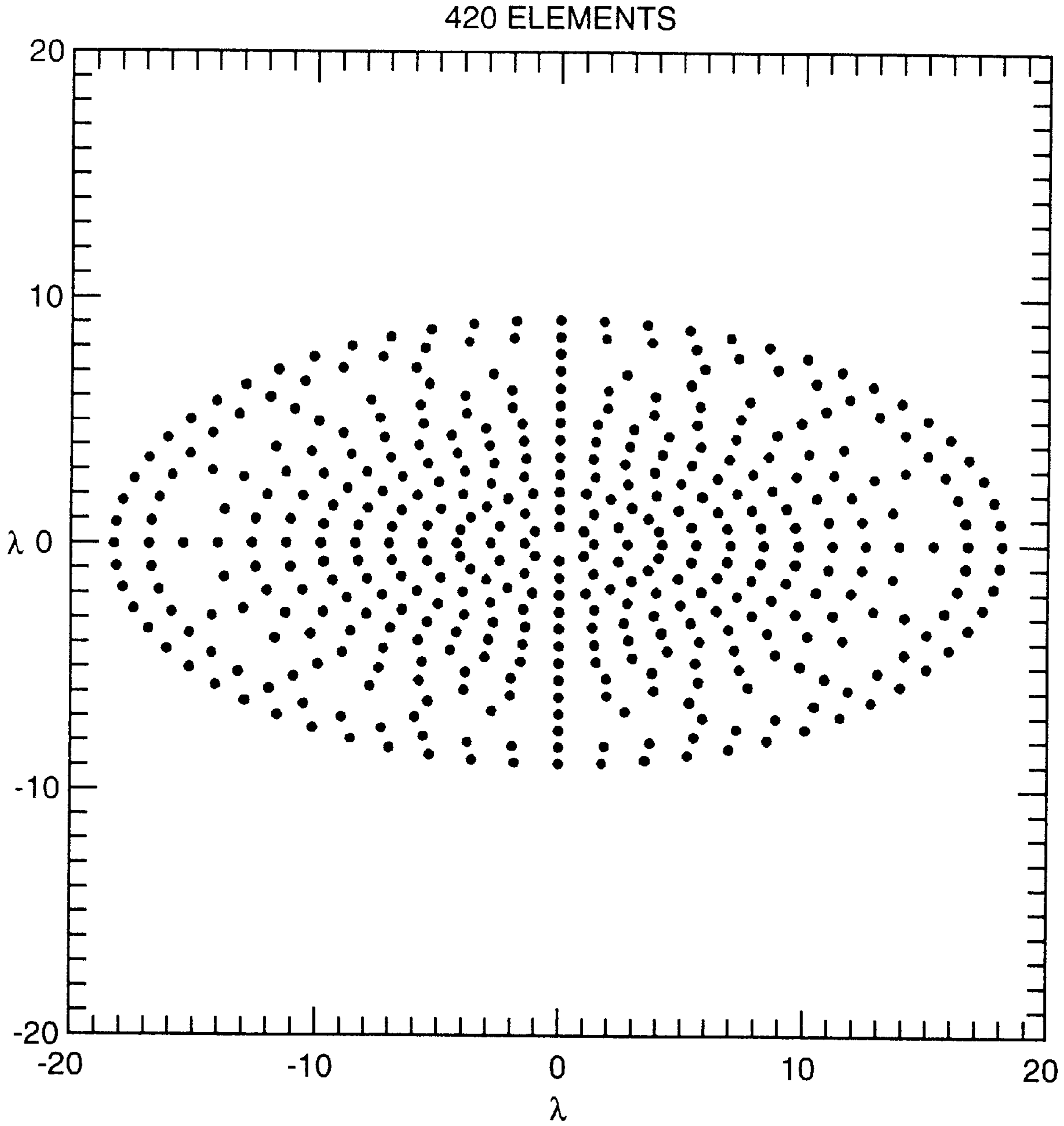
Figure 11C:
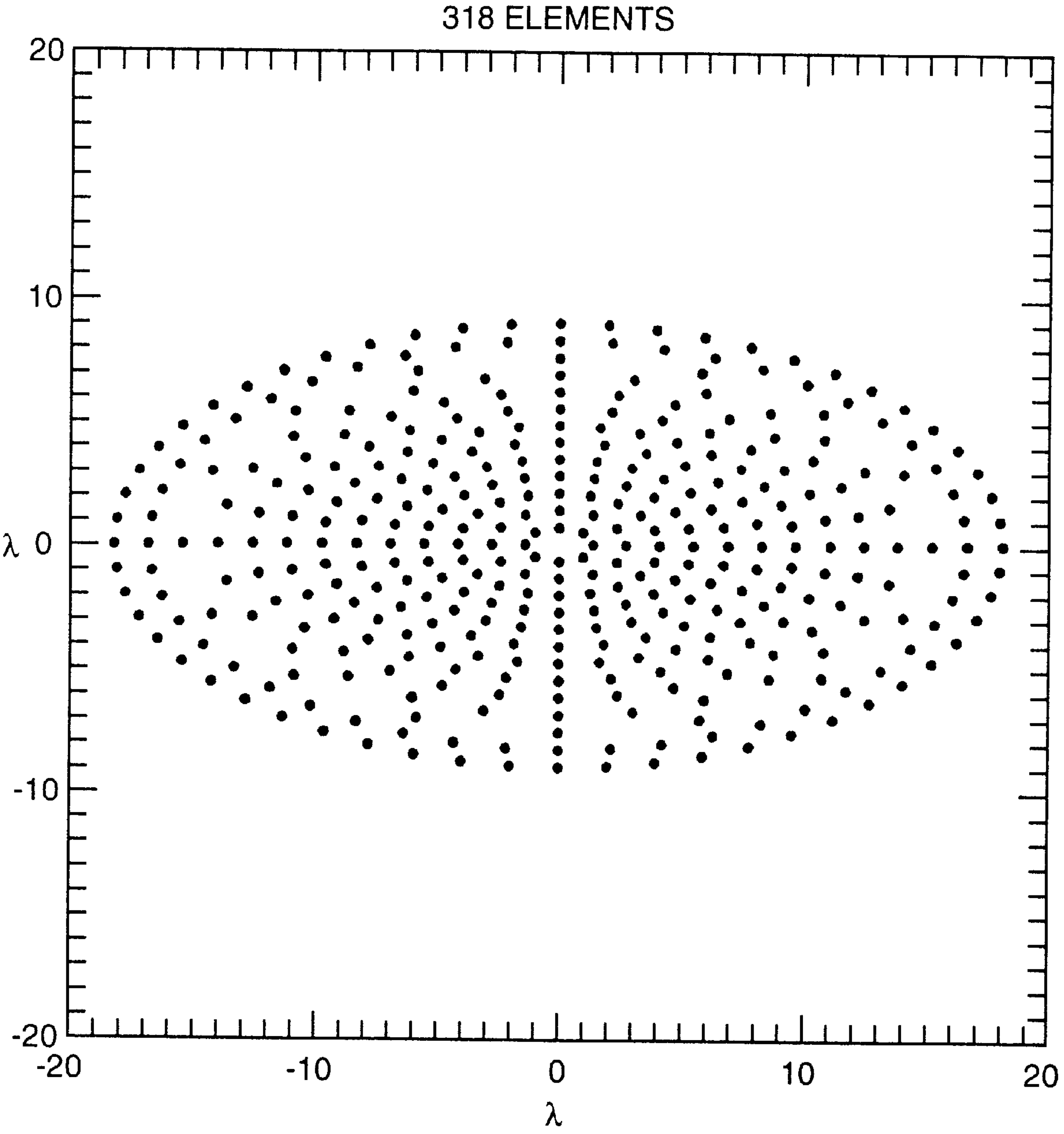
Figure 11D:
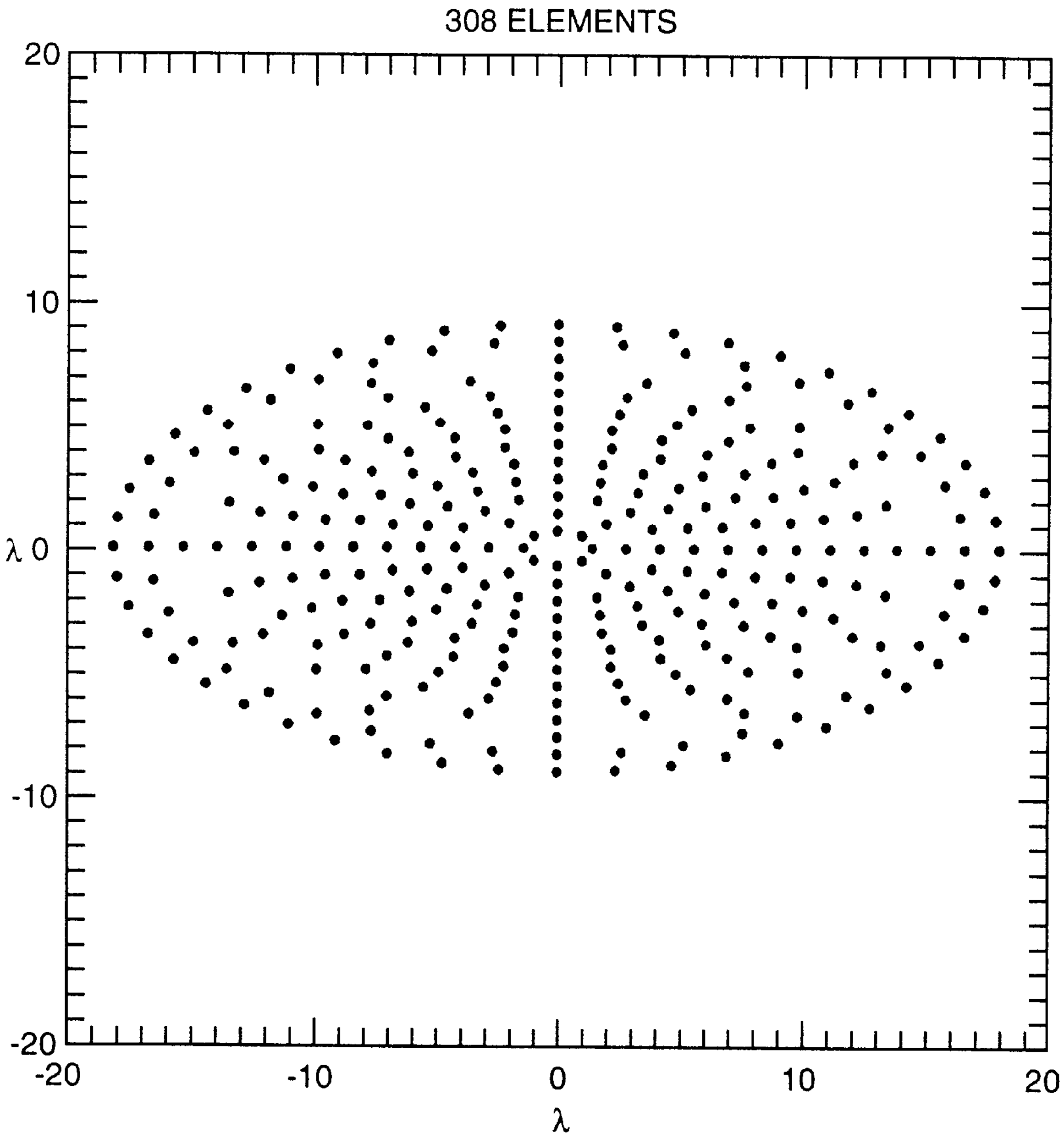
Figure 11E:
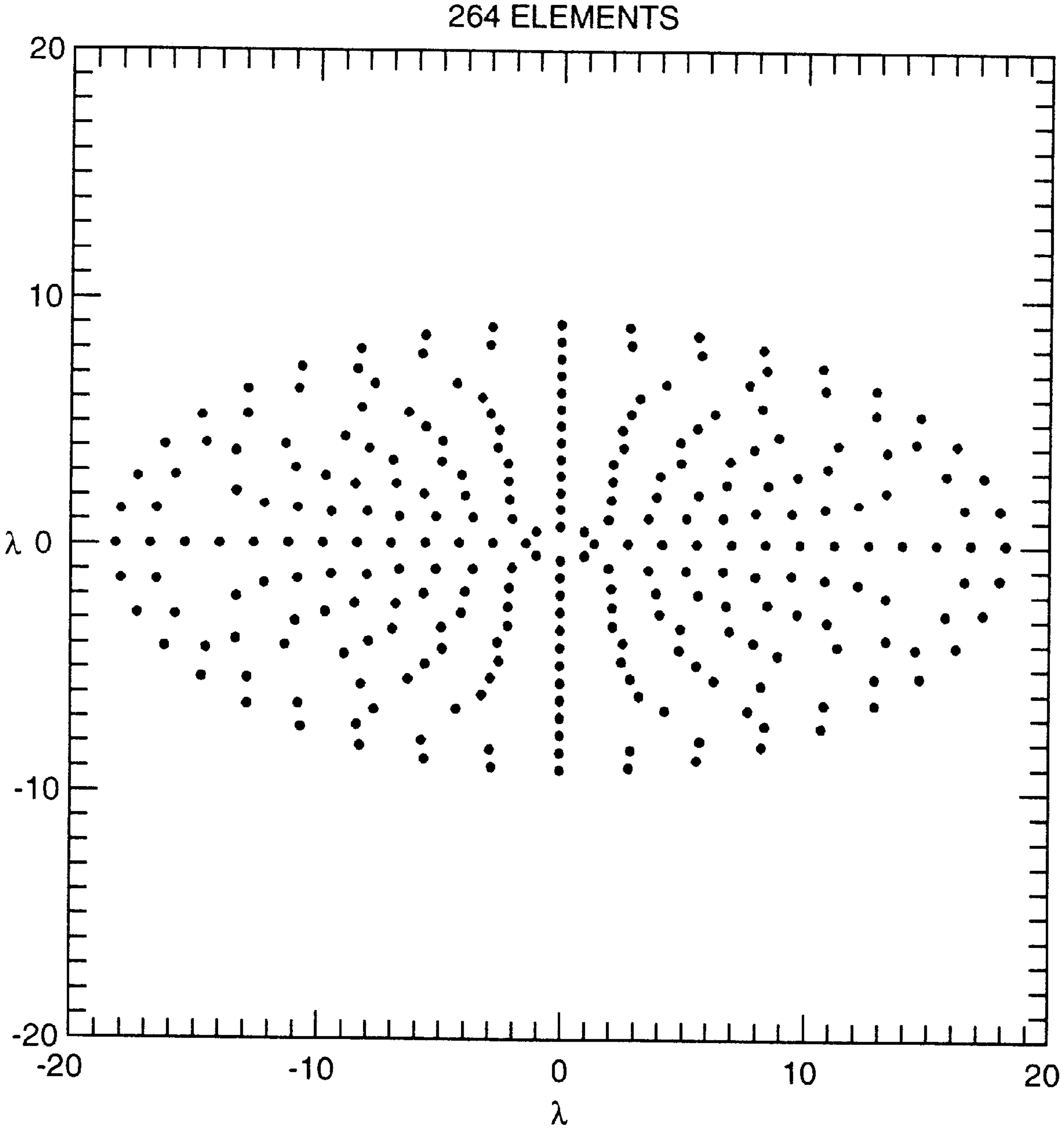
Figure 12A:
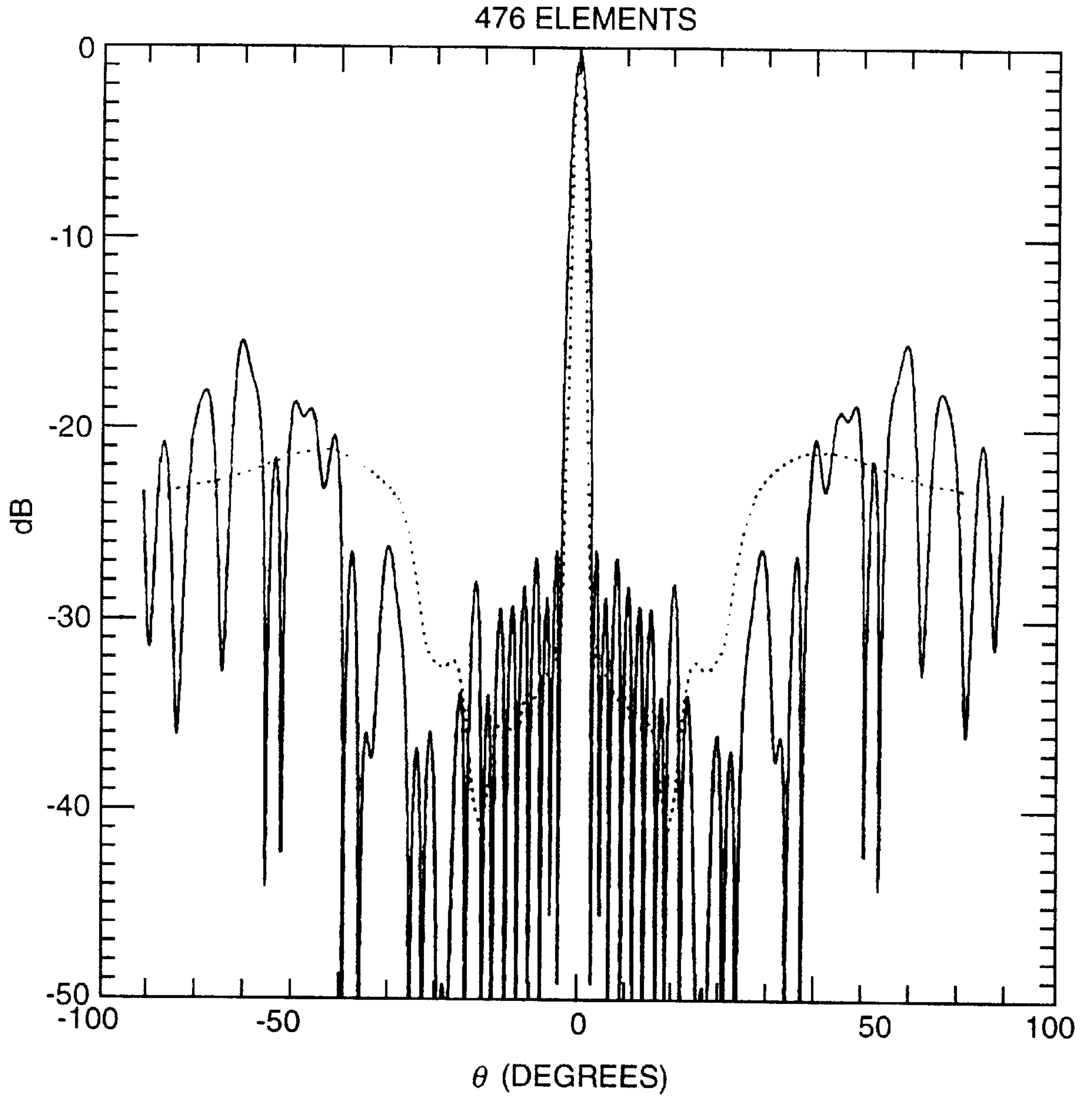
Figure 12B:
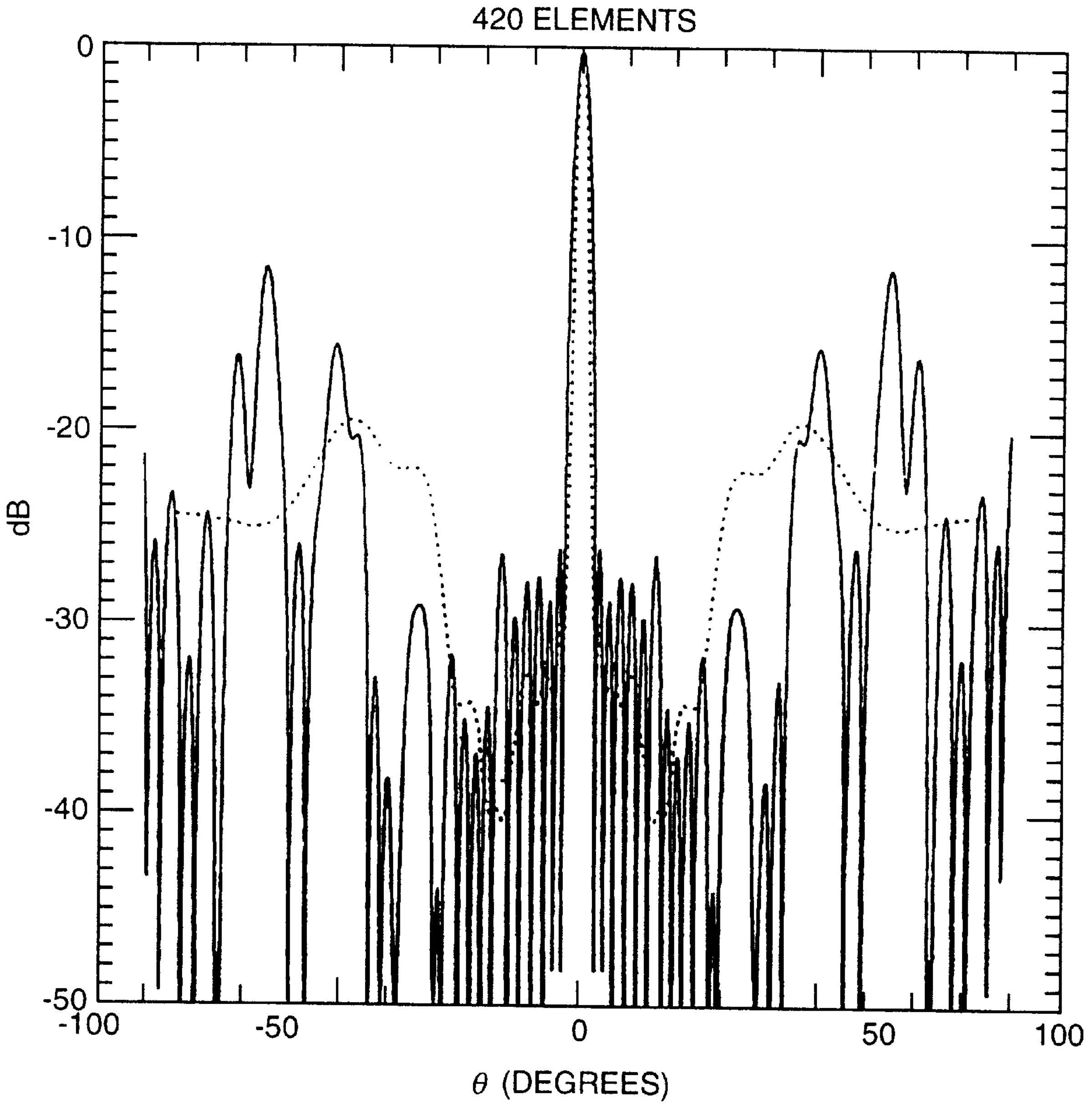
Figure 12C:
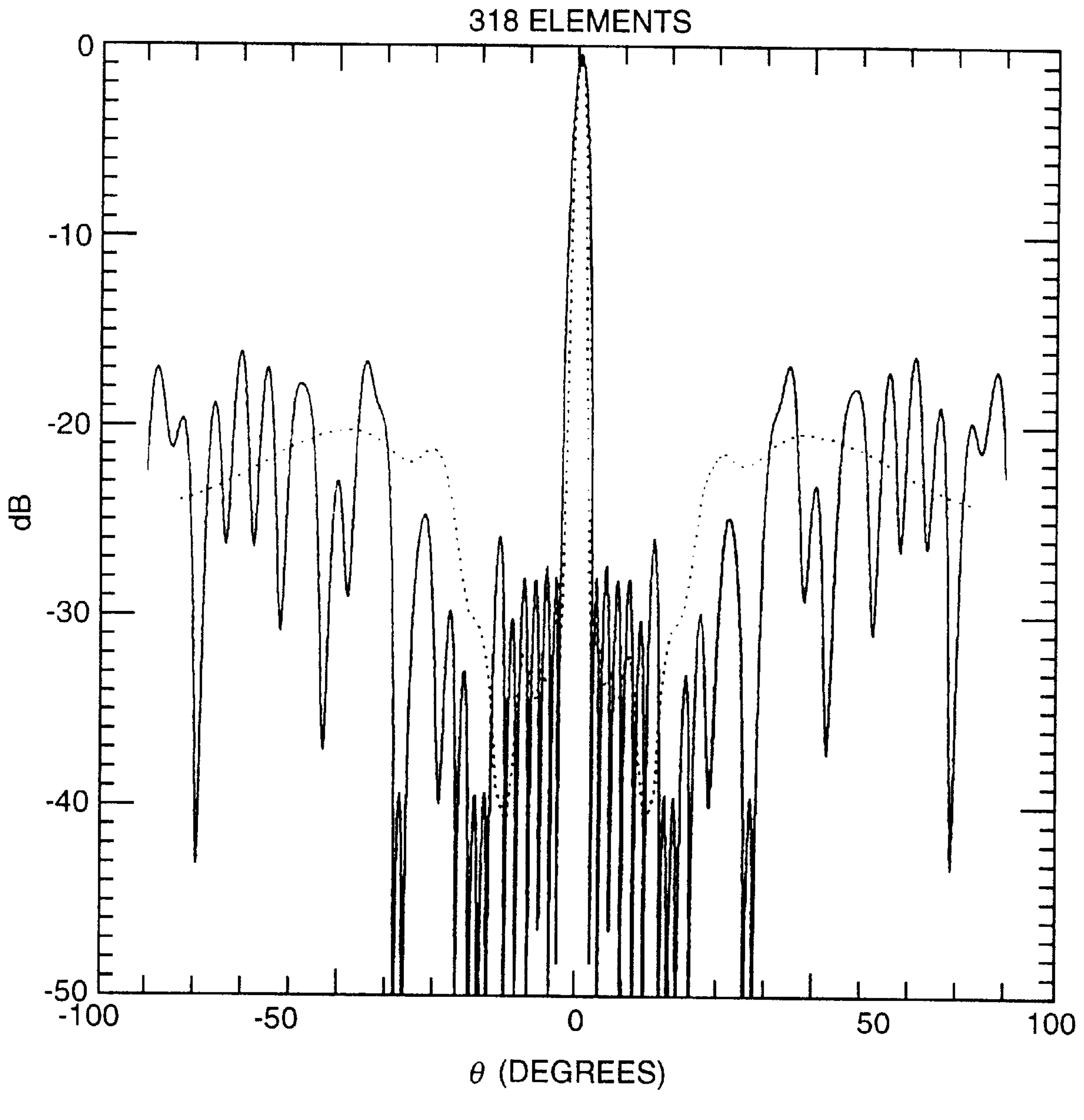
Figure 12D:
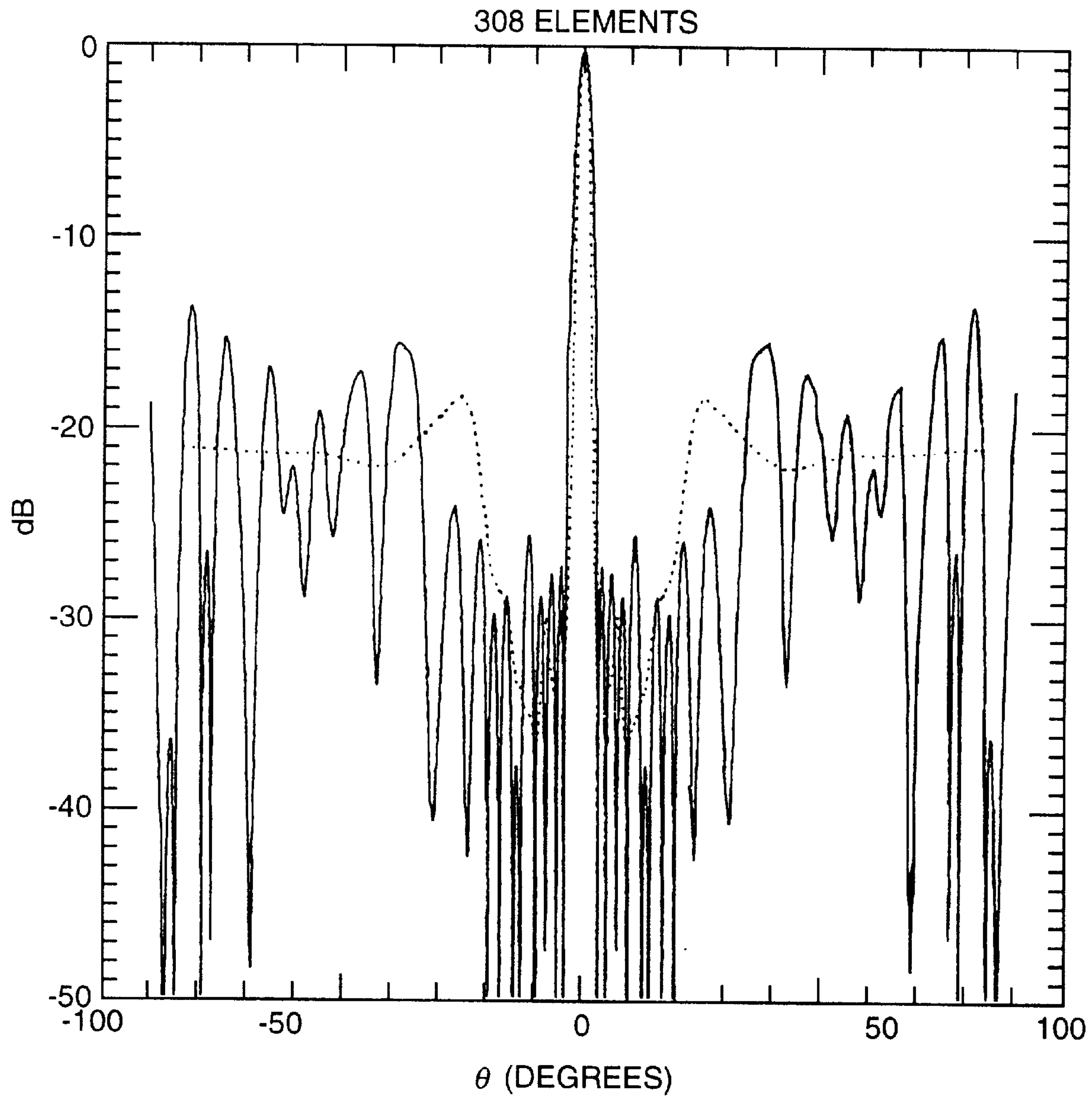
Figure 12E:
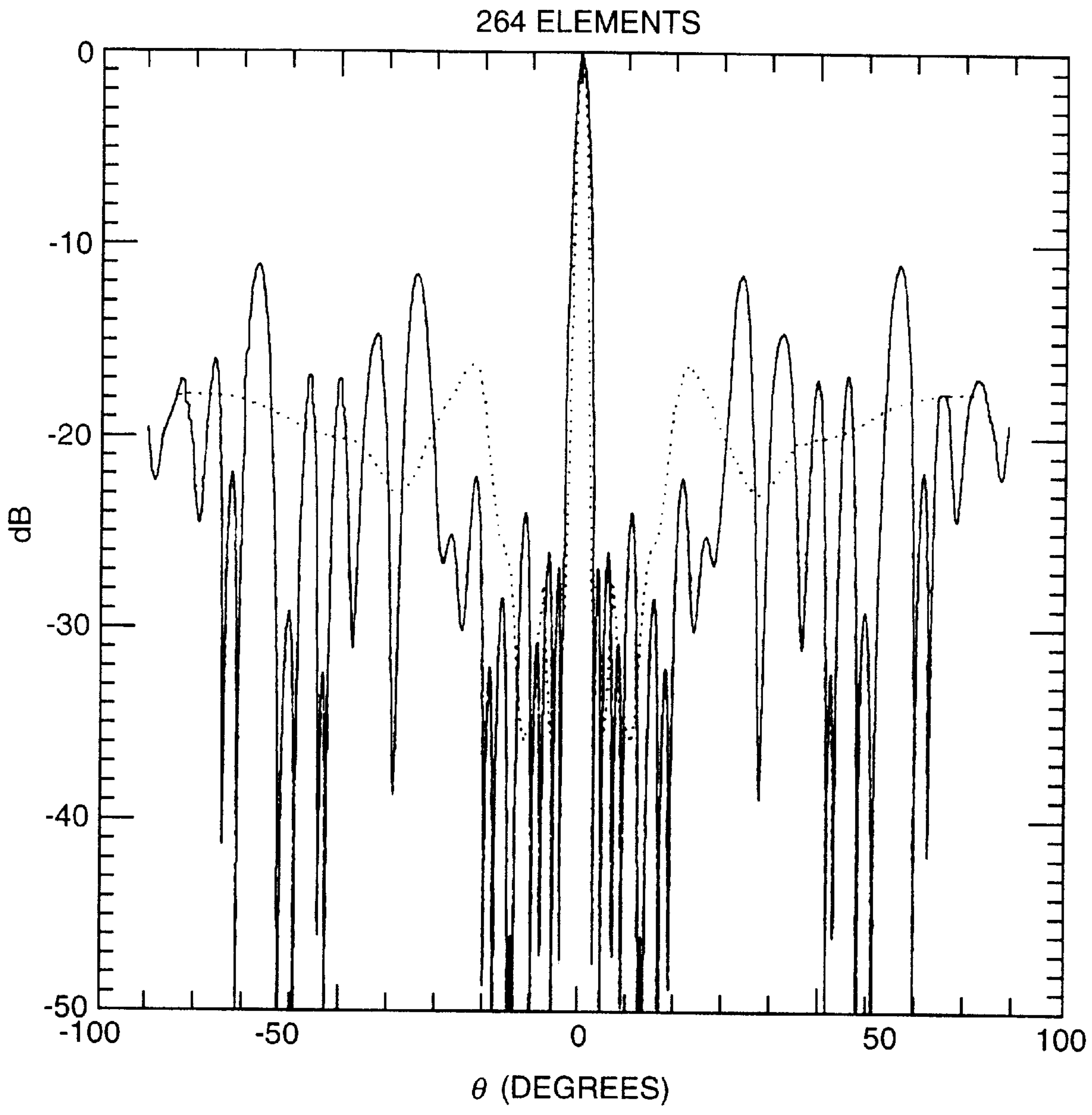

Numerical simulations were performed to demonstrate applicability of the theory to broadband pulses which are typical of a medical ultrasound imaging system. The simulation was for a true time-delay beamformer, with a single focus range for simplicity. The time delay beamformer simulation employed a frequency of 5 MHz and a sampling frequency of 500 MHz. FIG. 10 illustrates a typical pulse used for the simulation.

Figure 6A:
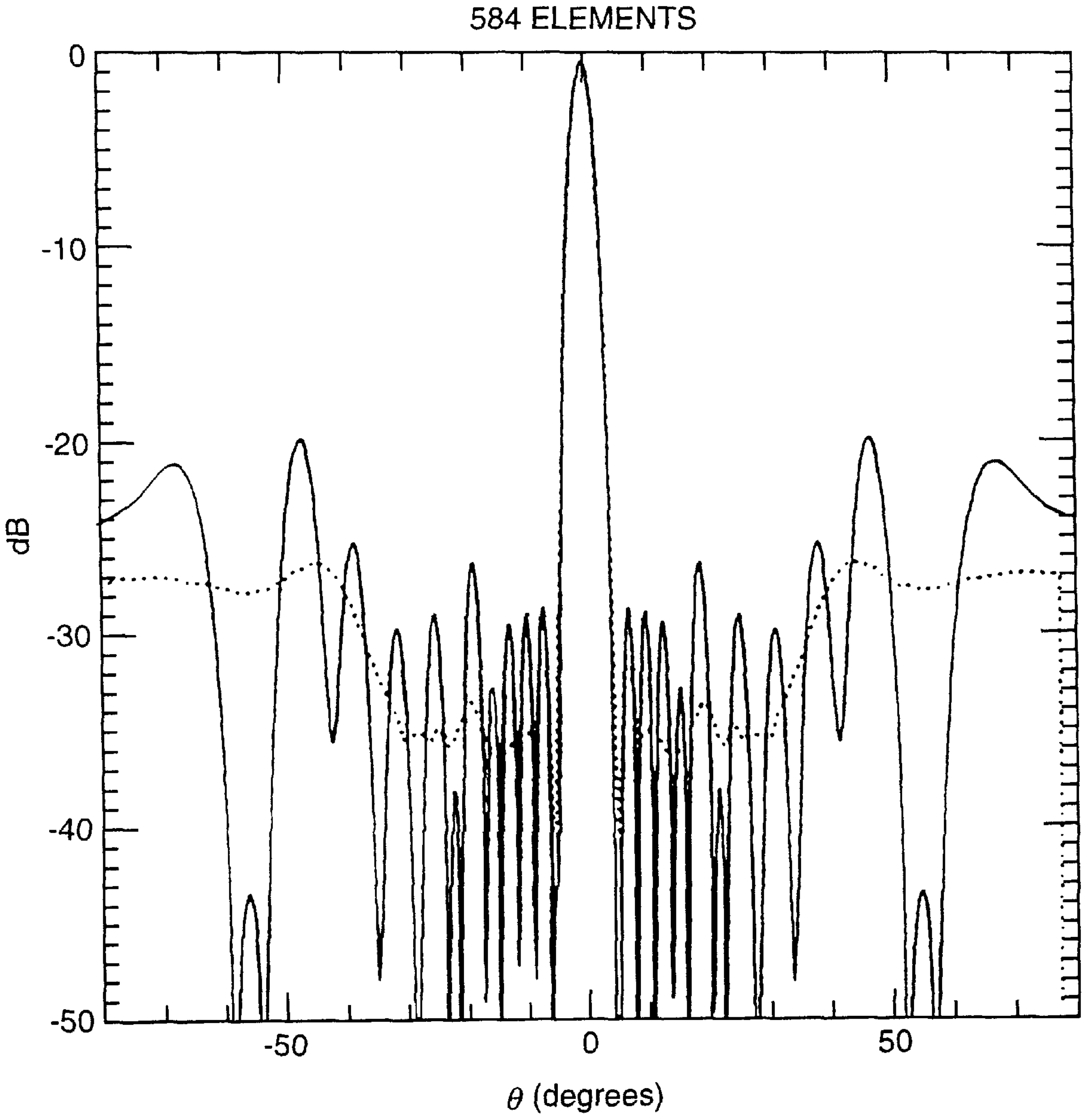
FIGS. 6A–6C are graphs showing the power patterns for both narrowband and wideband operation of the transducer array shown in FIGS. 5A–5C.
Figure 6B:
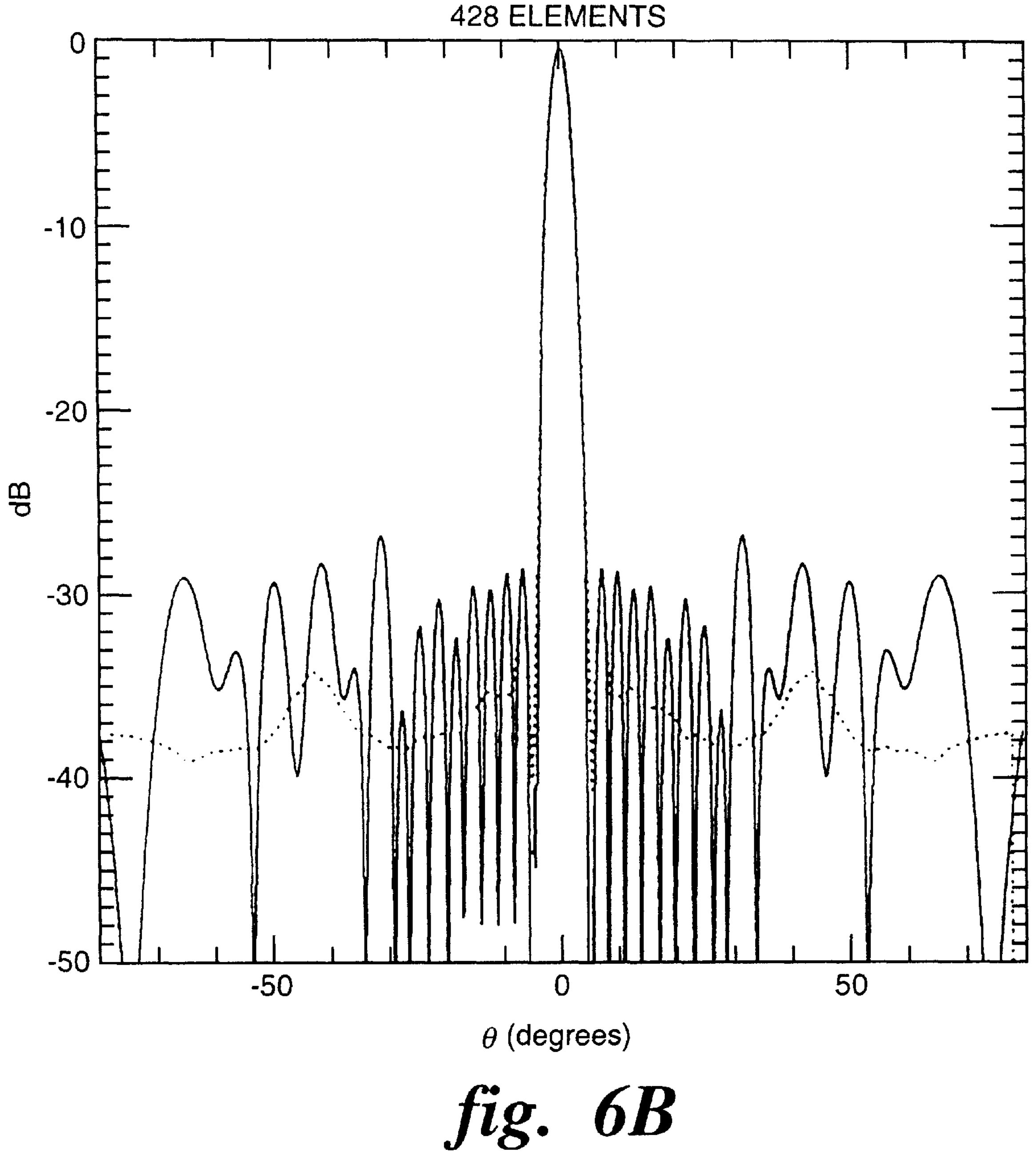
Figure 6C:
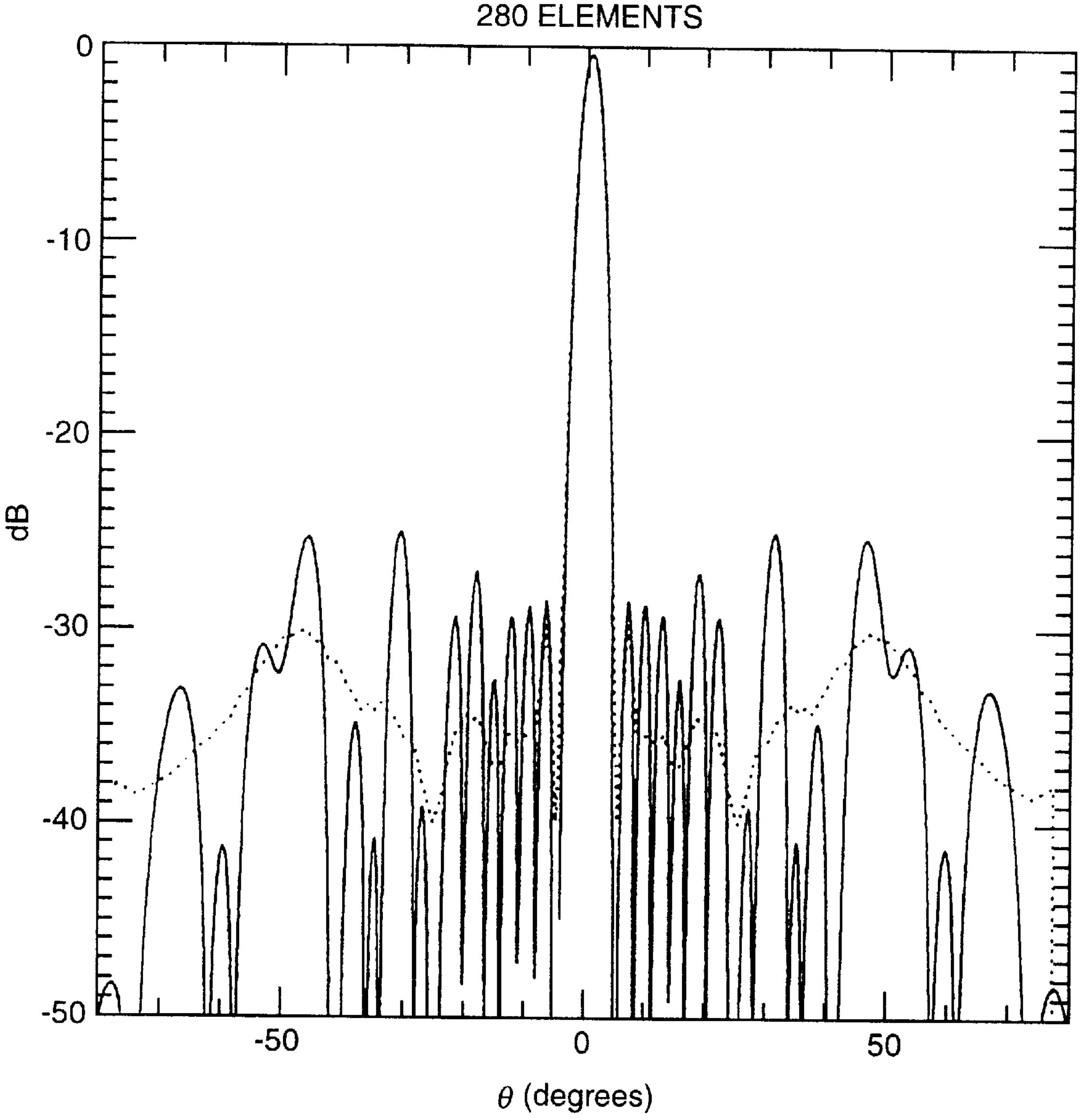
Figure 6D:
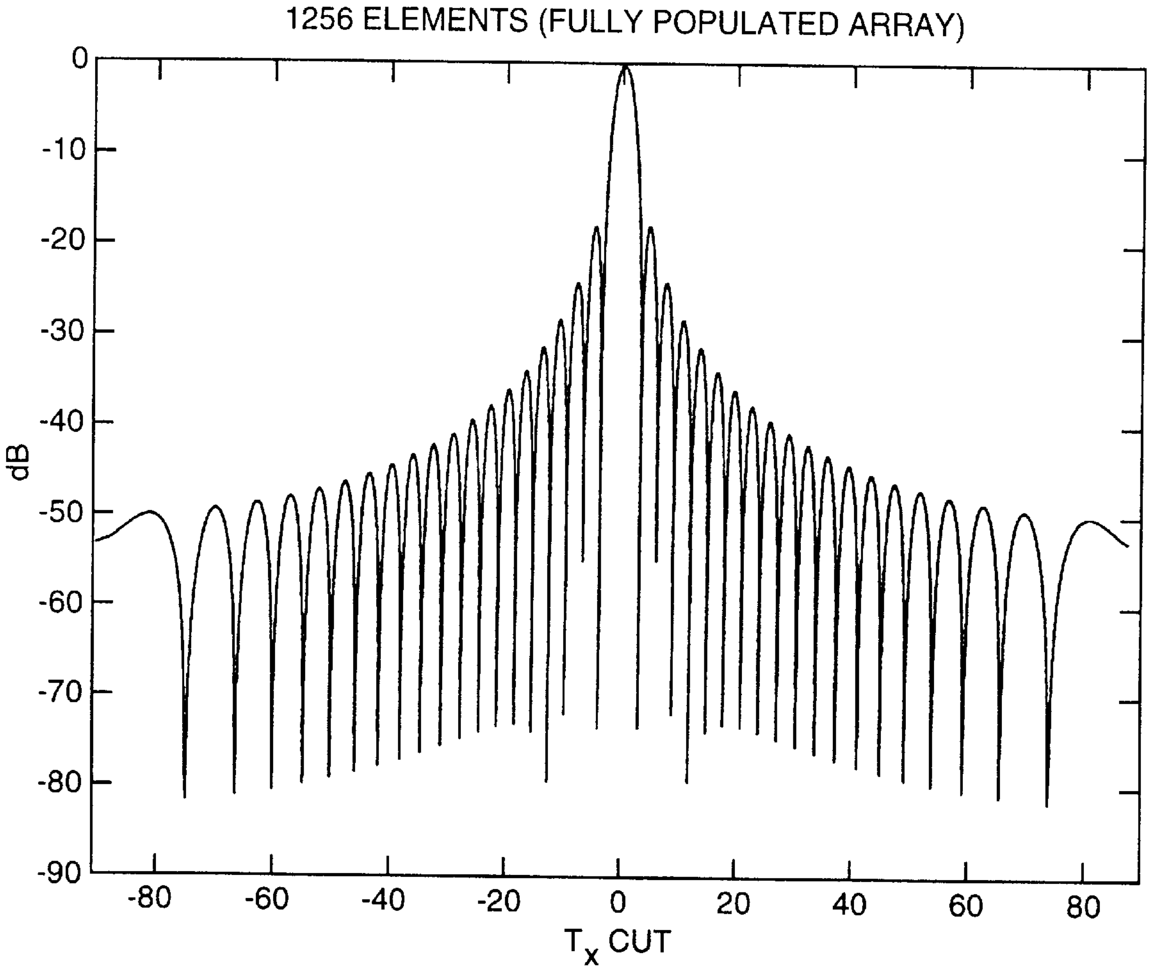
FIG. 6D is a graph showing the power pattern for narrowband operation for a fully populated circular aperture having 1256 elements.

For the thinned circular arrays shown in FIGS. 5A–5C, the corresponding patterns for various cuts are shown in FIGS. 6A–6C. The solid lines show performance at the center frequency (narrowband) and the dotted lines show the simulation results for pulsed operation to simulate ultrasound imaging (wideband). The cuts are made at ϕ=0° (FIG. 6A), 30° (FIG. 6B) and 45° (FIG. 6C). It can be seen that under both conditions, sidelobes are well below −20 dB. FIGS. 6A–6C can be compared with the pattern for a fully populated aperture having 1256 elements, shown in FIG. 6D.

Figure 7:
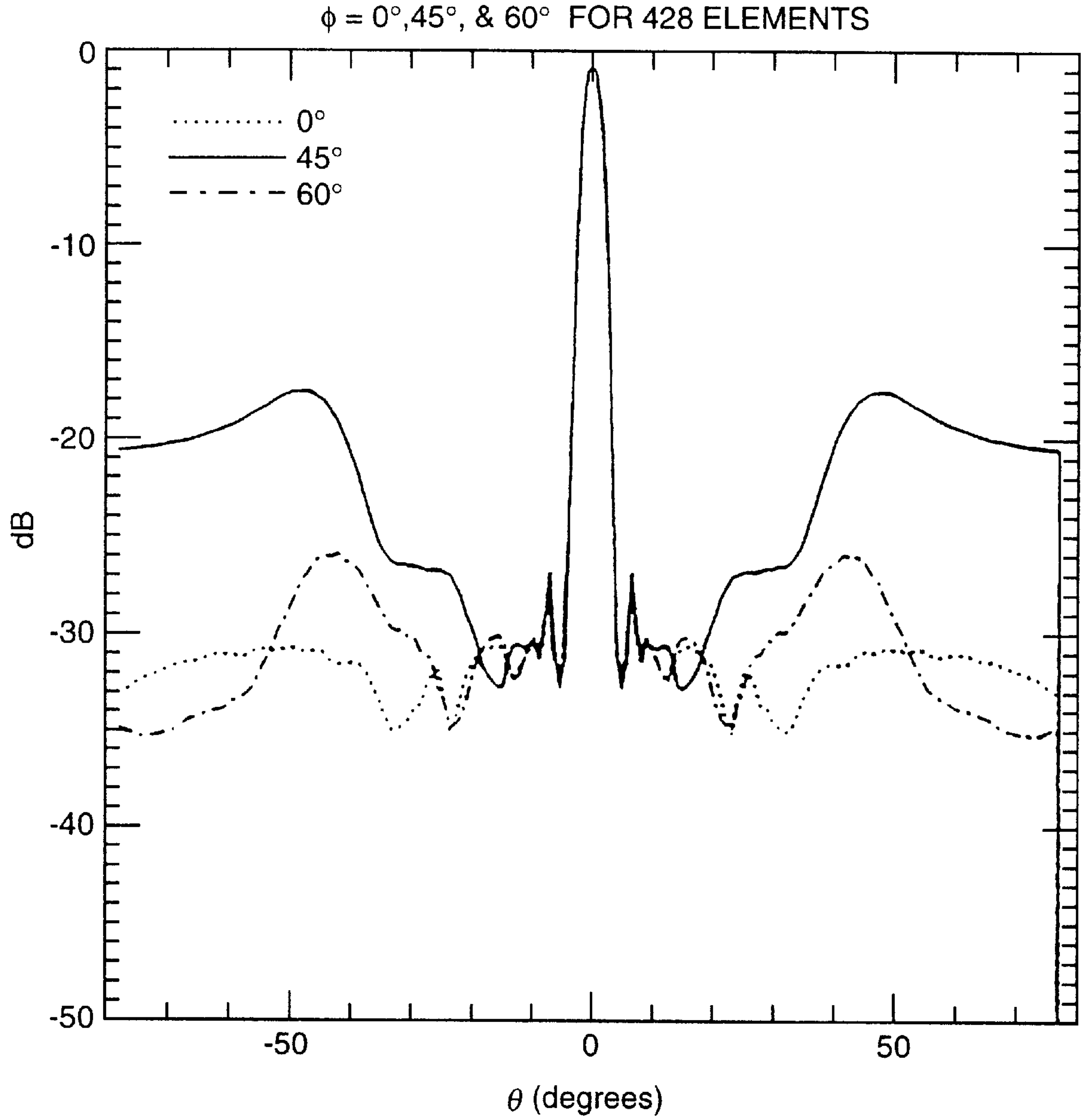
FIG. 7 is a graph comparing different power pattern cuts for a sparse transducer array of circular aperture with 428 transducer elements for wideband operation.

FIG. 7 compares different power pattern cuts for wideband operation for a sparse transducer array of circular aperture having 428 elements. The cuts are made at ϕ=0° (dotted line), 45° (solid line) and 60°.

Figure 8:
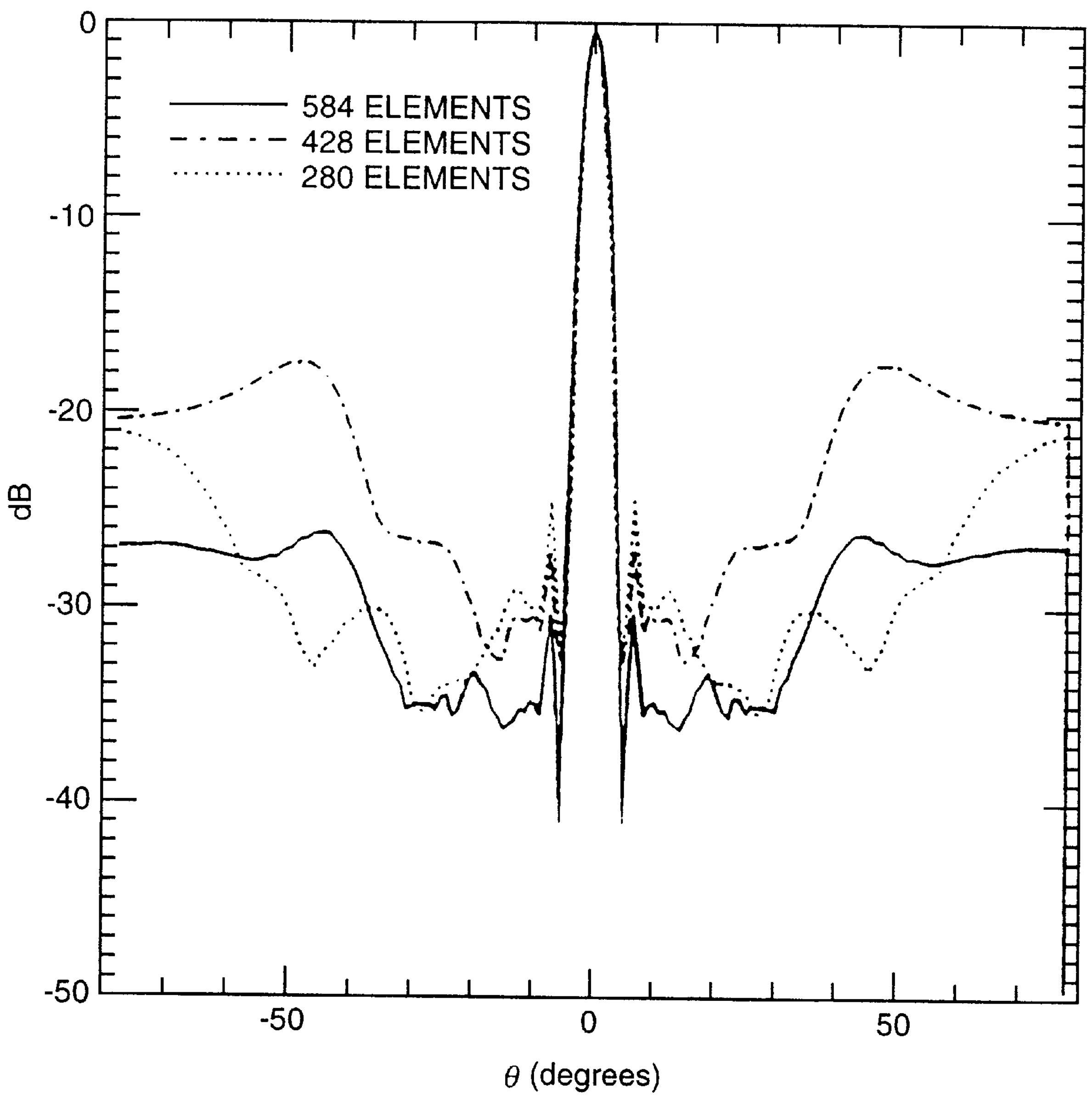
FIG. 8 is a graph comparing the power patterns for wideband operation for a circular aperture for different degrees of thinning.

FIG. 8 compares wideband power patterns for a circular aperture with thinning; 584 (solid line), 428 (dash-dot line) and 280 elements (dotted line). The cuts are made at (ϕ=0° for 584 elements and 45° for 280 and 428 elements.

Figure 9:
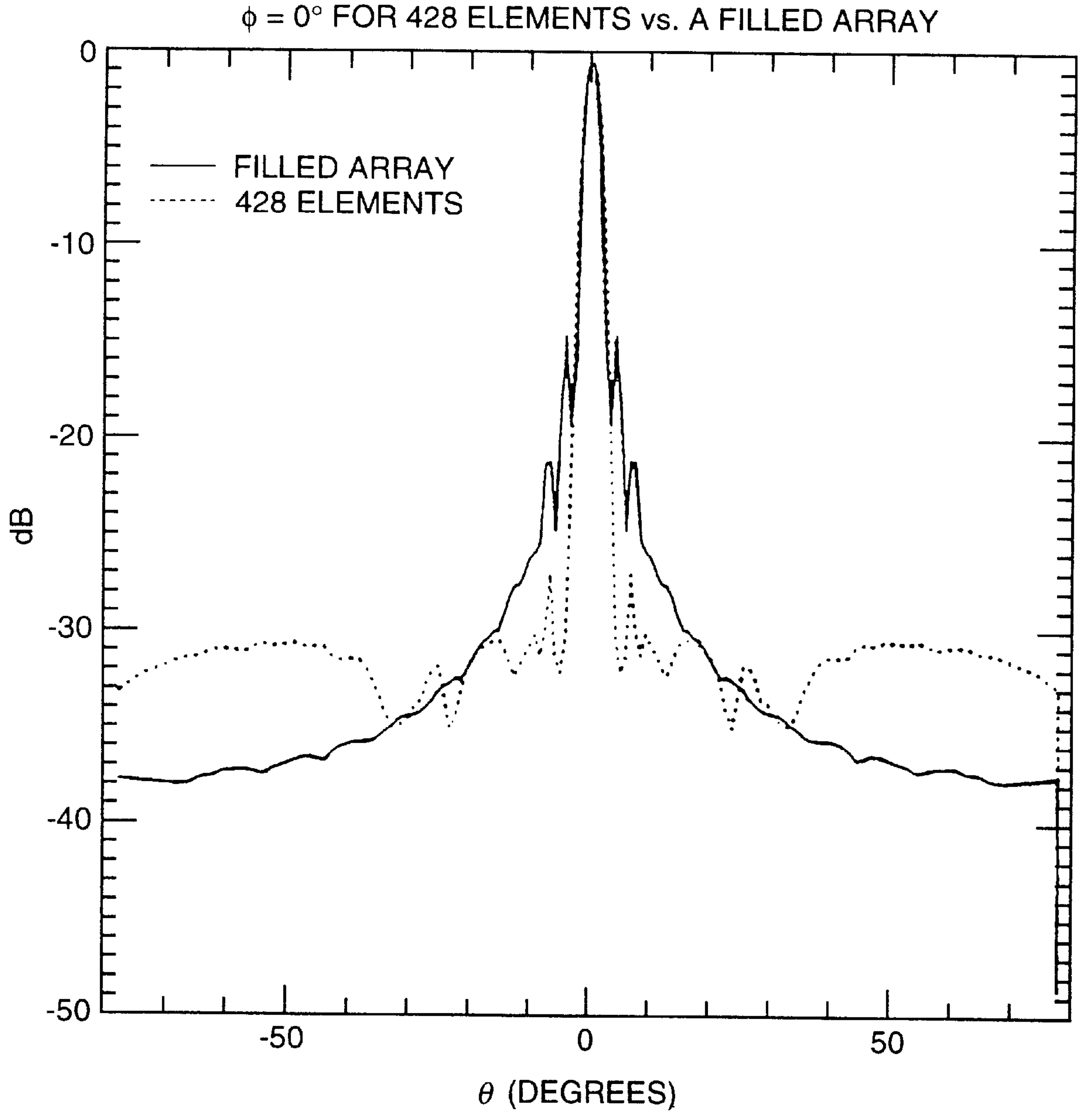
FIG. 9 is a graph showing the performance for wideband operation of a sparse array and a fully populated array of a circular aperture with 428 elements.

FIG. 9 is a graph showing the power patterns of a sparse array of circular aperture with 428 elements (dotted line) and a fully populated array (solid line). The cuts are made at ϕ=0° for both arrays.

FIGS. 11A–11E depict the location of transducer elements in a sparse array for an elliptical aperture having 476, 420, 308, 308 and 264 elements, respectively. FIGS. 12A–12E show the power patterns for both narrowband and wideband operation of the transducer arrays shown in FIGS. 11A–11E. The solid lines represent performance for narrowband operation and the dotted lines represent performance for wideband operation. Again it is apparent that the sidelobes are well-controlled.

Using the foregoing procedures, thinned two-dimensional arrays of transducer elements can be designed for use in ultrasound imaging systems. The design method of the invention can be applied to a variety of shapes consisting of self-similar geometric curves (see FIG. 2). In accordance with the invention, thinning is accomplished with sidelobe control. The design controls the near-in sidelobes, suppresses average sidelobes to a low level, and accomplishes thinning in the neighborhood of 50% or greater, without any appreciable degradation of the whole pattern and controlled sidelobes.

The procedure for designing an ultrasound imaging transducer, and the equations to be used, are summarized as follows:

(1) Select major and minor axes of the aperture to be designed. For a circular aperture, the major and minor axes are the same. This will provide the value of M, the number of rings.

(2) Select a desired sidelobe ratio R and compute A from Eq. (14).

(3) Select $\bar{n}$ and compute $\sigma$ and $\omega_i$ from Eqs. (15), (16) and (17).

(4) Solve Eqs. (21), select $N_1$ and compute $N_m$, m=2, . . . , M, such that $$\sum_{m=1}^{M} N_m$$

is the desired number of elements in the array.

(5) Once the $N_m$ are determined, use Eqs. (10), (11a) and (11b) to determine the locations of the elements on each circular or elliptical ring.

(6) Move the element locations onto a regular grid.

A simple algorithm can be used to move each calculated element location to the nearest grid point. Elements which would be moved to a grid point which is already occupied are deleted. The shifting of elements to the nearest grid locations and deletion of duplicate elements causes small perturbations in the array response, but these will not cause any significant deterioration in the sidelobe control.

The invention is not limited to geometries in which the rings are equally spaced. For a general thinning and space tapering method, a designer would need to find the number of elements on each ring as well as to locate the position of the ring. This procedure can be done by an iterative process in which a set of ring locations is assumed; then after proceeding as indicated hereinabove, iterations around the assumed locations of the rings are performed by Newton's method.

Figure 13:
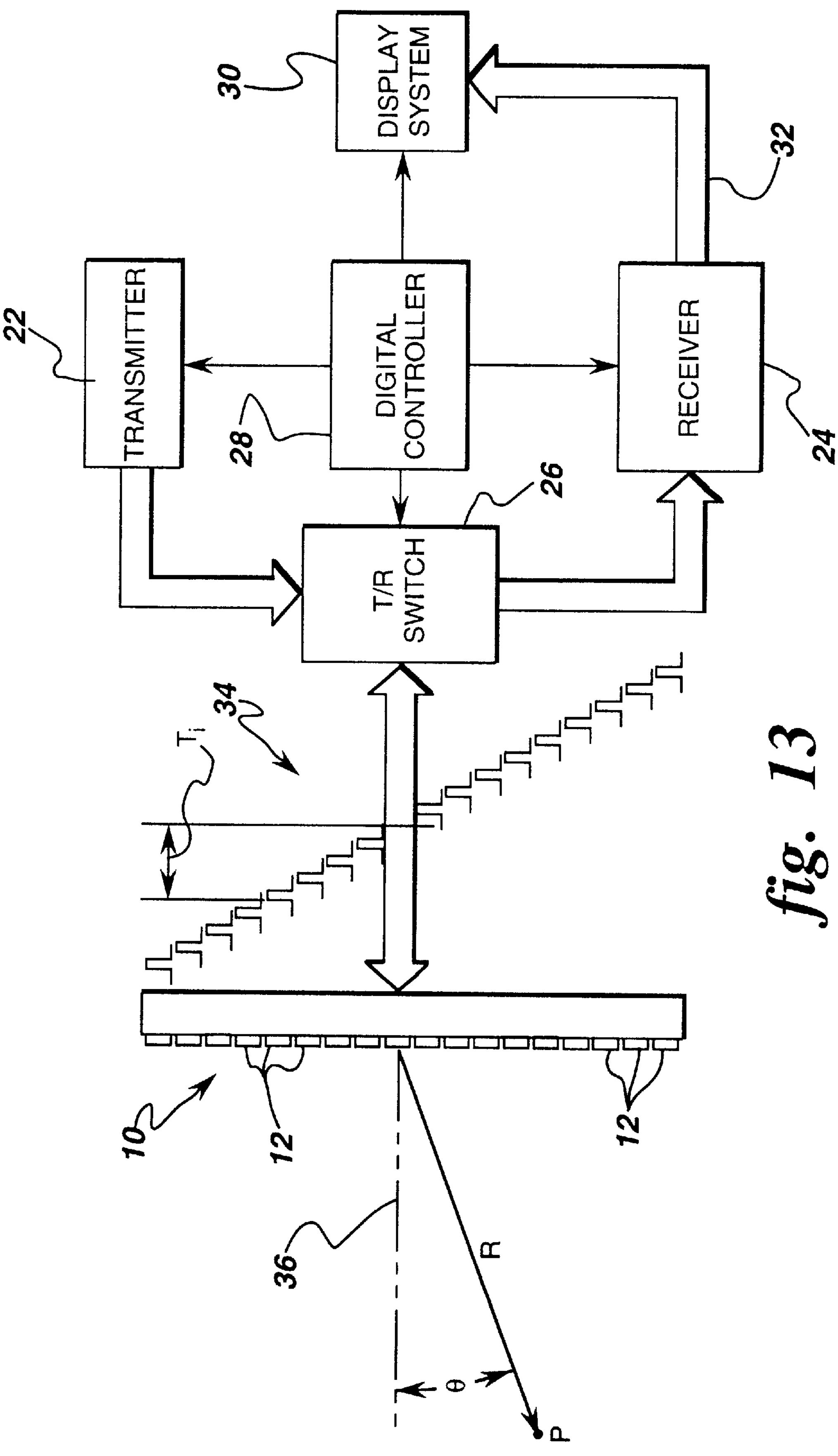
FIG. 13 is a block diagram of an ultrasound imaging system incorporating a sparse transducer array in accordance with the invention.

In accordance with the invention, a sparse transducer array is incorporated in an ultrasound imaging system. Such imaging system is depicted in FIG. 13 and includes a transducer array 10 comprised of a plurality of separately driven transducer elements 12, each of which produces a burst of ultrasonic energy when energized by a pulsed waveform produced by a transmitter 22. The ultrasonic energy reflected back to transducer array 10 from the object under study is converted to an electrical signal by each receiving transducer element 12 and applied separately to a receiver 24 through a set of transmit/receive (T/R) switches 26. Transmitter 22, receiver 24 and switches 26 are operated under control of a digital controller 28 responsive to commands by a human operator. A complete scan is performed by acquiring a series of echoes in which switches 26 are set to their transmit positions, transmitter 22 is gated ON momentarily to energize each transducer element 12, switches 26 are then set to their receive positions, and the subsequent echo signals detected by each transducer element 12 are applied to receiver 24, which combines the separate echo signals from each transducer element to produce a single echo signal which is used to produce a line in an image on a display monitor 30.

Transmitter 22 drives transducer array 10 such that the ultrasonic energy produced is directed, or steered, in a beam. To accomplish this, transmitter 22 imparts a time delay $T_i$ to the respective pulsed waveforms 34 that are applied to successive transducer elements 12. By adjusting the time delays $T_i$ appropriately in a conventional manner, the ultrasonic beam can be directed away from axis 36 by angles $\theta$ and $\phi$ and/or focused at a fixed range R. A sector scan is performed by progressively changing the time delays $T_i$ in successive excitations. The angles $\theta$ and $\phi$ are thus changed in increments to steer the transmitted beam in a succession of directions.

The echo signals produced by each burst of ultrasonic energy reflect from objects located at successive ranges along the ultrasonic beam. The echo signals are sensed separately by each transducer element 12 and a sample of the magnitude of the echo signal at a particular point in time represents the amount of reflection occurring at a specific range. Due to the differences in the propagation paths between a reflecting point P and each transducer element 12, however, these echo signals will not be detected simultaneously and their amplitudes will not be equal. Receiver 24 amplifies the separate echo signals, imparts the proper time delay to each, and sums them to provide a single echo signal which accurately indicates the total ultrasonic energy reflected from point P located at range R along the ultrasonic beam oriented at the angles $\theta$ and $\phi$.

While only certain preferred features of the invention have been illustrated and described, many modifications and changes will occur to those skilled in the art. It is, therefore, to be understood that the appended claims are intended to cover all such modifications and changes as fall within the true spirit of the invention.

We claim:

1. An ultrasound imaging system comprising:

an ultrasound transducer array comprising a grid having a predetermined number of grid points and a plurality of ultrasound transducer elements supported by said grid, each of said transducer elements being located at a respective grid point in a set of grid points selected to be located in a predetermined pattern so that an aperture of said array has smaller sidelobe levels than would be produced by a fully populated grid, the number of ultrasound transducer elements being less than said predetermined number;

transmitter means for activating said ultrasound transducer elements to transmit a series of transmit ultrasound waveforms;

beamforming means for forming receive beams from signals provided by said ultrasound transducer elements in response to reception of ultrasound energy from a reflecting point on which said transmit ultrasound waveforms impinge; and monitoring means for displaying an image which is a function of said receive beams.

2. The ultrasound imaging system of claim 1 wherein said predetermined pattern is symmetrical relative to a first axis of said aperture.

3. The ultrasound imaging system of claim 2 wherein said predetermined pattern is symmetrical relative to a second axis of said aperture perpendicular to said first axis.

4. The ultrasound imaging system of claim 1 wherein said aperture is generally circular in shape.

5. The ultrasound imaging system of claim 4, wherein each of said set of grid points is closest to a respective one of a set of calculated transducer locations, said set of calculated transducer locations comprising a plurality of subsets of calculated transducer locations, each of said subsets comprising a respective number of calculated transducer locations spaced along a respective one of a plurality of concentric circles.

6. The ultrasound imaging system of claim 1 wherein said aperture is generally elliptical in shape.

7. The ultrasound imaging system of claim 6 wherein each of said set of grid points is closest to a respective one of a set of calculated transducer locations, said set of calculated transducer locations comprising a plurality of subsets of calculated transducer locations, each of said subsets comprising a respective number of calculated transducer locations spaced along a respective one of a plurality of concentric elliptical rings.

8. An ultrasound transducer array for medical imaging, comprising:

a grid having a predetermined number of grid points; and a plurality of ultrasound transducers supported by said grid, each of said transducers being located at a respective grid point in a set of grid points arranged to form a non-circular aperture, the number of ultrasound transducers being less than said predetermined number, wherein the grid points of said set are located in a predetermined pattern so that said non-circular aperture of said array has smaller sidelobe levels than would be produced by a fully populated grid coextensive with said non-circular aperture.

9. The ultrasound transducer array of claim 8 wherein said predetermined pattern is symmetrical relative to a first axis of said aperture.

10. The ultrasound transducer array of claim 9 wherein said predetermined pattern is symmetrical relative to a second axis of said aperture perpendicular to said first axis.

11. The ultrasound transducer array of claim 8 wherein said non-circular aperture is generally elliptical in shape.

12. The ultrasound transducer array of claim 11 wherein each of said set of grid points is closest to a respective one of a set of calculated transducer locations, said set of calculated transducer locations comprising a plurality of subsets of calculated transducer locations, each of said subsets comprising a respective number of calculated transducer locations spaced along a respective one of a plurality of concentric elliptical rings.

* * * * *